United States Patent
Berman et al.

(10) Patent No.: US 10,280,451 B2
(45) Date of Patent: May 7, 2019

(54) DETECTION OF GENOME EDITING

(71) Applicants: Bio-Rad Laboratories, Inc., Hercules, CA (US); J. David Gladstone Institutes, San Francisco, CA (US)

(72) Inventors: Jennifer Berman, San Carlos, CA (US); Samantha Cooper, Berkeley, CA (US); George Karlin-Neumann, Palo Alto, CA (US); Yuichiro Miyaoka, San Francisco, CA (US); Bruce Conklin, San Francisco, CA (US); Josh Shinoff, Emeryville, CA (US)

(73) Assignees: Bio-Rad Laboratories, Inc., Hercules, CA (US); J. David Gladstone Institutes, San Francisco, CA (US)

( * ) Notice: Subject to any disclaimer, the term of this patent is extended or adjusted under 35 U.S.C. 154(b) by 516 days.

(21) Appl. No.: 14/991,818

(22) Filed: Jan. 8, 2016

(65) Prior Publication Data
US 2016/0208319 A1    Jul. 21, 2016

Related U.S. Application Data

(60) Provisional application No. 62/101,828, filed on Jan. 9, 2015, provisional application No. 62/201,446, filed on Aug. 5, 2015.

(51) Int. Cl.
| | | |
|---|---|---|
| *C12Q 1/68* | (2018.01) |
| *C12Q 1/6827* | (2018.01) |
| *C12Q 1/6809* | (2018.01) |
| *C12N 15/10* | (2006.01) |
| *C12N 15/63* | (2006.01) |

(52) U.S. Cl.
CPC ......... *C12Q 1/6827* (2013.01); *C12N 15/102* (2013.01); *C12N 15/63* (2013.01); *C12Q 1/6809* (2013.01)

(58) Field of Classification Search
None
See application file for complete search history.

(56) References Cited

U.S. PATENT DOCUMENTS

| | | |
|---|---|---|
| 6,777,187 B2 | 8/2004 | Makarov et al. |
| 2006/0068394 A1 | 3/2006 | Langmore et al. |
| 2013/0217131 A1 | 8/2013 | Kim |
| 2014/0357530 A1 | 12/2014 | Zhang et al. |

FOREIGN PATENT DOCUMENTS

| | | |
|---|---|---|
| WO | 2013/142578 A1 | 9/2013 |
| WO | 2014/022702 A2 | 2/2014 |
| WO | 2014/151511 A2 | 9/2014 |

OTHER PUBLICATIONS

Wang et al. (Cell, 2013, 153:910-918) (Year: 2013).*
Taly et al. (Trends in Molecular Medicine, 2012, 18(7):405-416) (Year: 2012).*
International Search Report and Written Opinion dated Mar. 17, 2016 for PCT/US2016/012748, 10 pages.

(Continued)

*Primary Examiner* — Stephanie K Mummert
(74) *Attorney, Agent, or Firm* — Kilpatrick Townsend and Stockton LLP

(57) ABSTRACT

Methods, compositions, and kits are provided for quantification of genome editing.

21 Claims, 19 Drawing Sheets

Specification includes a Sequence Listing.

(56) References Cited

OTHER PUBLICATIONS

Aubert et al., "In vitro Inactivation of Latent HSV by Targeted Mutagenesis Using an HSV-specific Homing Endonuclease," *Molecular Therapy—Nucleic Acids*, 3:e146 (Feb. 2014) 12 pages.
Forster et al., "Genome editing 101: let's go digital," *Nature Methods*; 11(3):248-249 (Mar 2014).
Granahan et al., "CRISPR/Cas-9: An Exciting Addition to Genomic Editing," *Life Sciences Law & Industry Report*, Mar. 2014 (5 pages).
Hendel et al., "Quantifying Genome-Editing Outcomes at Endogenous Loci with SMRT Sequencing," *Cell Reports*, 7:293-305 (Apr. 2014).
Kay et al., "Engineering Cellular Resistance to HIV," *New Engl. J. Med.* 370:968-969 (Mar 2014).
Kim et al., "A guide to genome engineering with programmable nucleases," *Nature Reviews Genetics*, 15:321-334 (May 2014).
Miyaoka et al., "Isolation of single-base genome-edited human iPS cells without antibiotic selection," *Nature Methods*; 11(3):291-293 (Mar. 2014) (7 pages, includes Online Methods).
Pennisi, E., "The CRISPR Craze," *Science*, 341:833-836 (Aug. 2013).
Tebas et al., "Gene Editing of CCR5 in Autologous CD4 T Cells of Persons Infected with HIV," *New Engl. J. Med.*, 370(10):901-910 (Mar. 2014).
Unknown, "Puzzle on How Cas9 Targets and Cleaves DNA Solved," *Genetic Engineering & Biotechnology News*, Jan. 30, 2014 (2 pages).
Yang et al., "Targeted and genome-wide sequencing reveal single nucleotide variations impacting specificity of Cas9 in human stem cells," *Nature Communications*, 5:5507 doi:10.1038/ncomms6507 (Oct. 2014) 6 pages.
Extended European Search Report in EP Application No. 16735521.3 dated Jun. 28, 2018; 9 pages.
Certo, M. et al.; "Tracking genome engineering outcome at individual DNA breakpoints"; *Nature Methods*; vol. 8, No. 8; Aug. 1, 2011; pp. 671-677; Nature Publishing Group, New York, NY.
Guschin D.Y. et al.; "A Rapid and General Assay for Monitoring Endogenous Gene Modification"; *Methods in Molecular Biology*; vol. 649, pp. 247-256; Humana Press, Inc., US.

\* cited by examiner

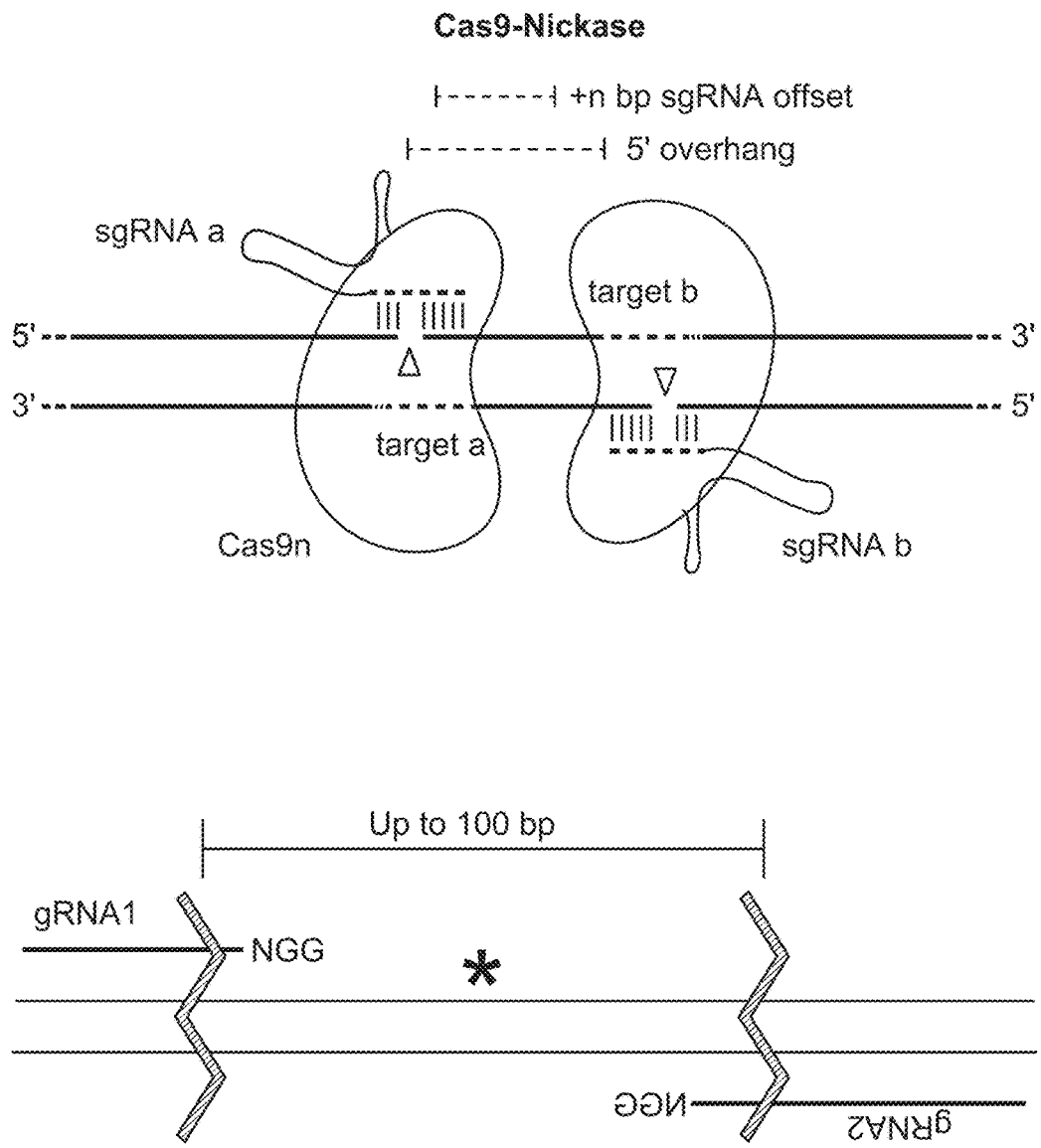
FIG. 2 (Cont. 1)

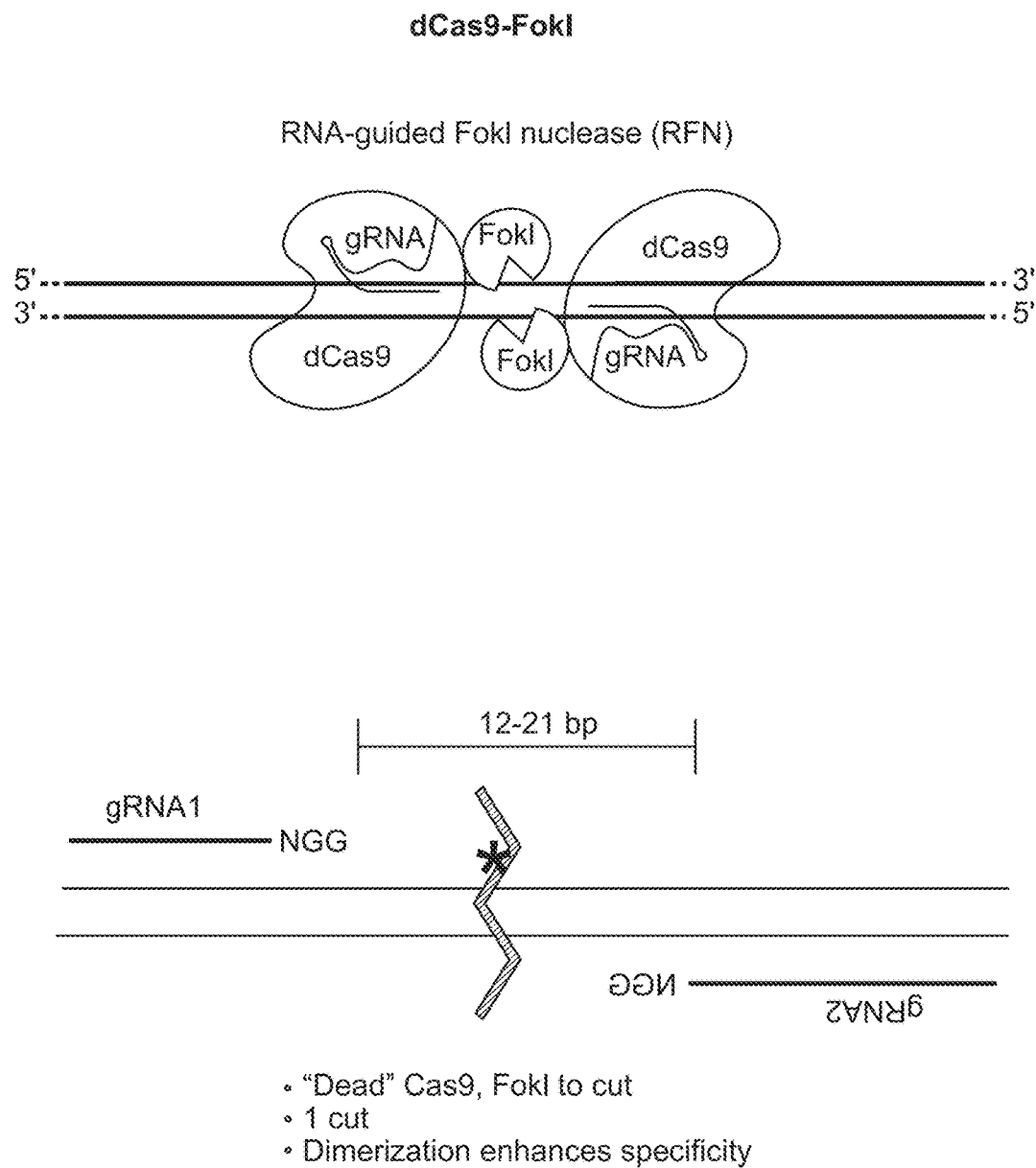
FIG. 2 (Cont. 2)

Schematic of everything
----------------------- hhhhhhhhhhhh - rough hex probe location
ffffffffffff - rough fam probe location

Probe positions (approx)

```
                                    hhhhhhhhhhhhhh  hhhhhhhhhhhh
                                                    ffffffffffff
                                                    ffffffffffff
```

HDR or NHEJ positions (approx)
```
                         99                    FF                    H
```

Donor oligo
```
                    SEQ ID NO:4 acagATATGGCCCAGAAAGGCCGGTCTaGTAGTCC
SEQ ID NO:5 ccttggctccctggctccctggctccctcacagATATGG              GGTCTCGTAGTCC
SEQ ID NO:6 GGTCTCGTAGTCC
``` gRNA positions (approx)
SEQ ID NO:7 taaatcctgctccttggctccctggctccctcacagATATGGCCCAGAAAGGCCGCGGTCTCGTAGTCC

Example: RBM20 R636S probe & primer positions (for all 3 strategies combined):

Primer                               HEX (NHEJ)
SEQ ID NO:8 GTCCTCTGCACGGAAG         SEQ ID NO:9 tgctccttggctccct          SEQ ID NO:10 ccgcggtctagtagtcc   FAM (HDR)
SEQ ID NO:12 gtcctctgcacggaagccaga ... taaatcctgctccttggctccctcacagATATGGCCCAGAAAGGCCGGGTCTCGTAGTCC
SEQ ID NO:13 caggagacgtgccttcggtct ... atttaggacgaggaaccgaggagtgtcTATACCGGGTCTTTCCGGCGCCAGAGCATCAGG
                                         SEQ ID NO:16 CCGGGTCTTTCCGGC      HEX (NHEJ)

FIG. 6

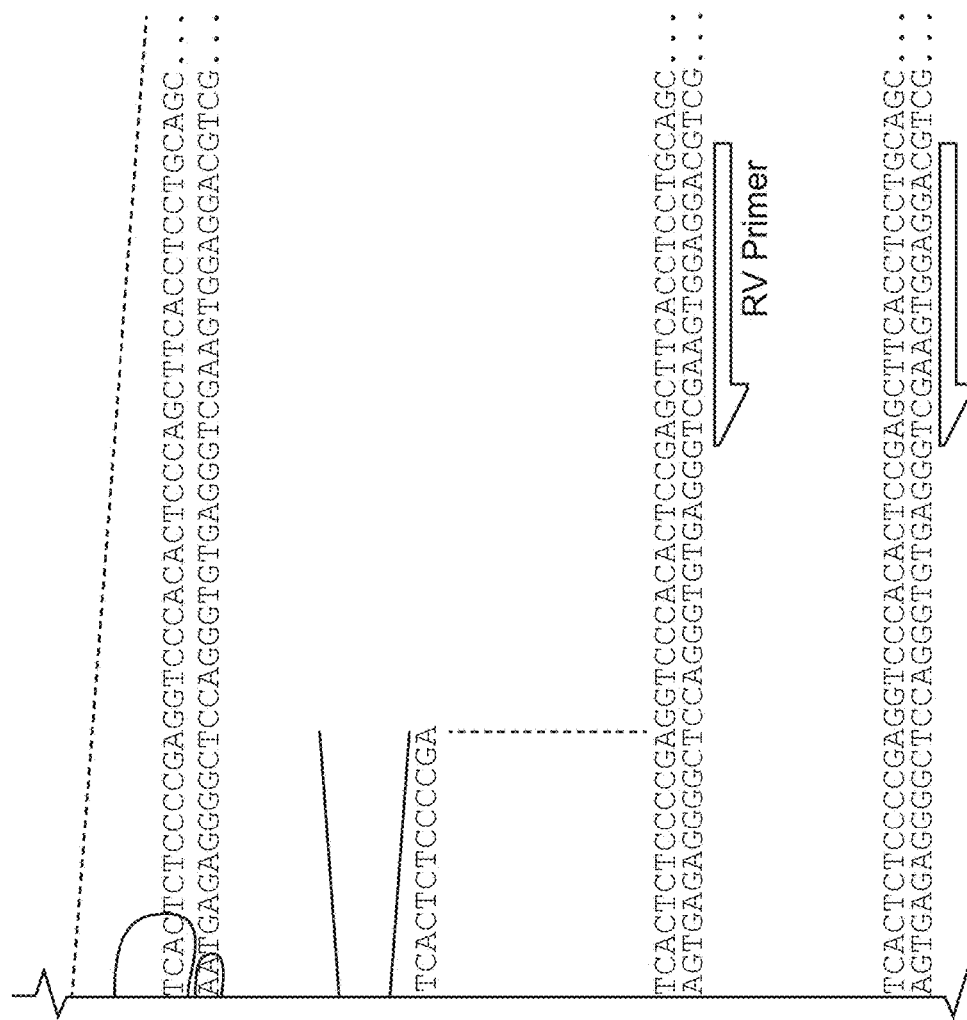

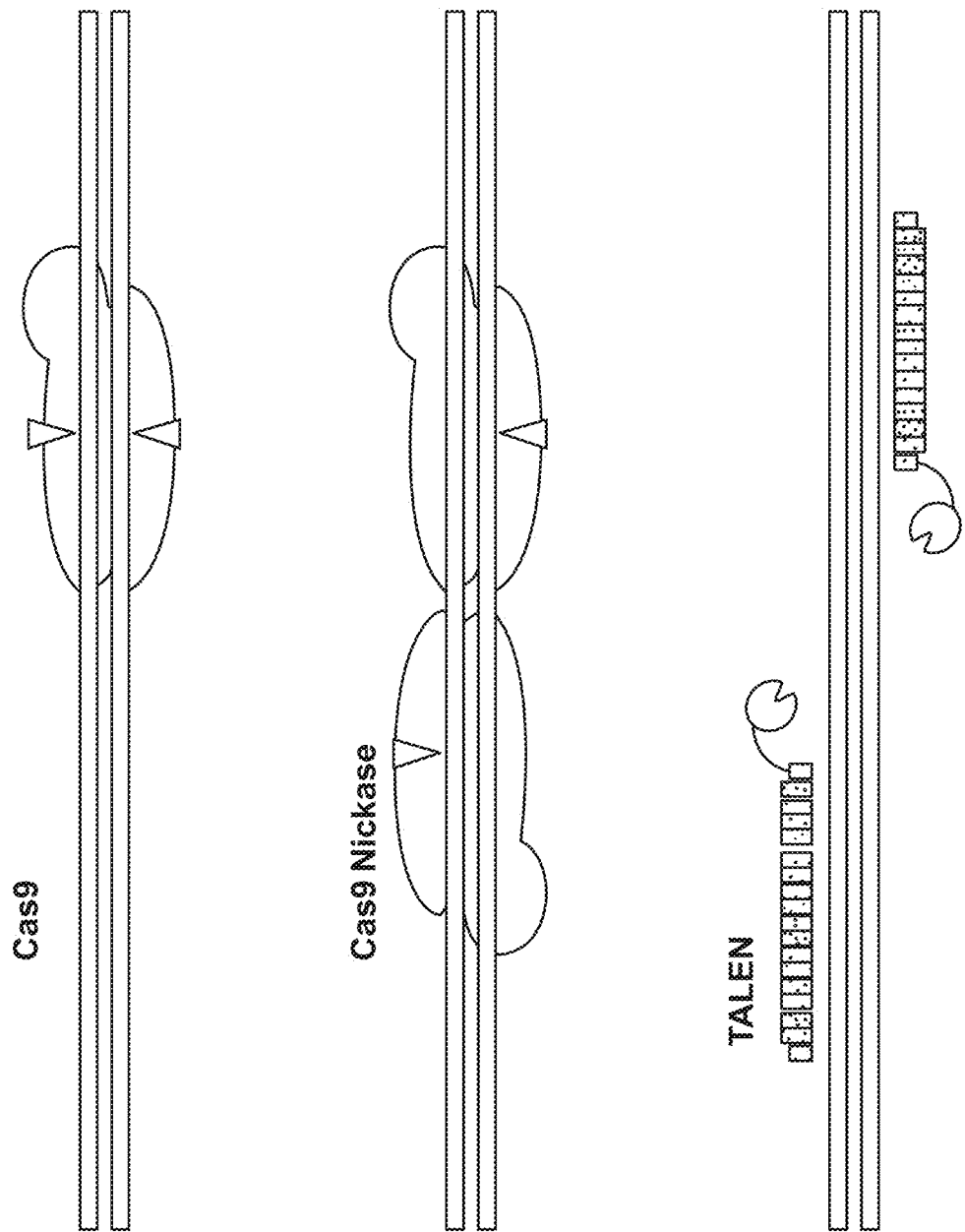

DETECTION OF GENOME EDITING

CROSS-REFERENCE TO RELATED PATENT APPLICATIONS

This application claims priority to US Provisional Application No. 62/101,828, filed Jan. 9, 2015 and U.S. Provisional Application No. 62/201,446, filed Aug. 5, 2015, each of which are incorporated by reference.

STATEMENT AS TO RIGHTS TO INVENTIONS MADE UNDER FEDERALLY SPONSORED RESEARCH AND DEVELOPMENT

This invention was made with government support under grants HL 100406 and HL098179 awarded by the National Institutes of Health. The government has certain rights in this invention.

REFERENCE TO SUBMISSION OF A SEQUENCE LISTING

This application includes a Sequence Listing as a text file named "0968420_ST25.txt" created Jan. 8, 2016 and containing 9,080 bytes. The material contained in this text file is incorporated by reference in its entirety for all purposes.

BACKGROUND OF THE INVENTION

Methods and compositions for genome editing are of great interest to the biotechnology and pharmaceutical community. Indeed, the ability to precisely edit genomes can be considered a rate limiting step for the development of a wide variety of therapeutic applications. Recent technologies have expanded the number of tools available for genome editing. Such tools include zinc finger nucleases (See, e.g., Kim et al., Proc Natl Acad Sci USA. 1996 Feb. 6; 93(3): 1156-60); transcription activator-like effector nucleases (TALENS) (See, e.g., Miller et al., Nat Biotechnol. 2011 February; 29(2):143-8); CRISPR-Cas (See, e.g., Mali et al., Nat Methods. 2013 October; 10(10):957-63) nucleases; and nickase versions thereof.

BRIEF SUMMARY OF THE INVENTION

In one aspect, the present invention provides a method for simultaneous quantification of homology directed repair (HDR) and non-homologous end joining (NHEJ) genome editing products in a sample of cells, wherein said sample of cells has been contacted with a site-specific genome editing reagent configured to cleave or nick DNA in a target genomic region and an HDR template nucleic acid, or the sample of cells comprises cells that have been contacted with a site-specific genome editing reagent configured to cleave or nick DNA in a target genomic region the method comprising: a) forming a plurality of mixture partitions having an average volume, wherein the mixture partitions comprise: i) the target genomic region; ii) a DNA-dependent DNA polymerase; iii) a forward and a reverse oligonucleotide amplification primer, wherein the forward and reverse primers hybridize to opposite strands of, and flank, the target genomic region, and wherein the primers are configured to amplify the target genomic region in the presence of the polymerase; iv) a detectably labeled oligonucleotide reference probe, wherein the reference probe hybridizes to a wild-type target genomic region, a target genomic region containing an HDR mutation introduced by homology directed repair of DNA damage from the site specific genome editing reagent, and a target genomic region containing an NHEJ mutation introduced by NHEJ repair of DNA damage from the site specific genome editing reagent; v) a detectably labeled oligonucleotide HDR probe, wherein the HDR probe hybridizes to the target genomic region containing the HDR mutation; and vi) a detectably labeled oligonucleotide NHEJ drop-off probe, wherein the NHEJ drop-off probe hybridizes to the wild-type target genomic region, and wherein the NHEJ drop-off probe does not hybridize to the target genomic region containing the NHEJ mutation; b) amplifying the target genomic region in the plurality of mixture partitions; and c) determining a quantity of wild-type target genomic regions, a quantity of target genomic regions containing an HDR mutation, and a quantity of target genomic regions containing an NHEJ mutation by detecting hybridization of the labeled probes to the target genomic regions in the plurality of mixture partitions.

In some embodiments, the sample of cells comprises cells that have been contacted with a site-specific genome editing reagent configured to cleave or nick DNA in a target genomic region and an HDR template nucleic acid. In some cases, at least a portion of the contacted cells have been edited by insertion of the HDR template nucleic acid into a cleavage site of the site-specific genome editing reagent via homology directed repair. In some embodiments, the sample of cells comprises cells that have been contacted with a site-specific genome editing reagent configured to cleave or nick DNA in a target genomic region (e.g., without contacting with an HDR template nucleic acid). In some cases, at least a portion of the contacted cells have been edited by non-homologous end joining repair at a cleavage site of the site-specific genome editing reagent.

In some embodiments, the reference and HDR probes comprise the same detectable label. In some embodiments, the HDR probe does not hybridize to the wild-type target genomic region. In some embodiments, the NHEJ drop off probe does not hybridize to the target genomic region containing the HDR mutation. In some embodiments, the NHEJ drop off probe hybridizes to the target genomic region containing the HDR mutation. In some embodiments, the DNA dependent DNA polymerase comprises 5' to 3' exonuclease activity and c) comprises detecting an increase in fluorescence caused by 5' to 3' exonuclease digestion of the hybridized labeled probes in the plurality of mixture partitions. In some embodiments, the plurality of mixture partitions further comprise an HDR dark oligonucleotide probe, wherein the HDR dark probe comprises a 3' end that is not extendable by the DNA polymerase, and wherein the HDR dark probe competes for hybridization of the HDR probe to the wild-type target genomic region.

In some embodiments, the NHEJ drop-off probe competes for hybridization of the HDR probe to the wild-type target genomic region. In some embodiments, the site-specific genome editing reagent is a CRISPR-Cas9 reagent, a TALEN, or a Zinc-Finger Nuclease. In some embodiments, the site-specific genome editing reagent comprises two site-specific genome nickases, wherein each nickase is configured to nick target DNA in the genome of a cell within less than about 1 kb of the other nickase. In some embodiments, the method comprises, before the forming the plurality of mixture partitions, providing the sample of cells that has been contacted with a site-specific genome editing reagent and extracting the target genomic regions. In some embodiments, the method comprises, before the forming the plurality of mixture partitions, providing the sample of cells and extracting the target genomic regions.

In some cases, the providing comprises contacting a plurality of cells with the site-specific genome editing reagent. In some cases, the plurality of cells contacted with the site-specific genome editing reagent are administered to a patient, and the providing comprises providing a sample of cells from the patient to which the cells have been administered. In some cases, the providing further comprises contacting the plurality of cells with an HDR template nucleic acid, wherein the HDR template nucleic acid comprises a mutation of a portion of the target genomic region and is configured to function as a template during homology directed repair of the target genomic region and thereby introduce the HDR mutation into the target genomic region. In some cases, the HDR template nucleic acid comprises DNA. In some cases, the HDR template nucleic acid is a single stranded DNA oligonucleotide.

In some embodiments, the plurality of mixture partitions comprise a plurality of structurally different detectably labeled oligonucleotide NHEJ drop-off probes, wherein the plurality of structurally different NHEJ drop-off probes hybridize to different sub-regions of the wild-type target genomic region. In some cases, the plurality of structurally different NHEJ drop off probes do not hybridize to NHEJ mutated sub-regions. In some cases, wherein the plurality of structurally different NHEJ drop off probes do not hybridize to NHEJ mutated sub-regions and do not hybridize to HDR mutated sub-regions. In some cases, wherein the plurality of structurally different NHEJ drop off probes do not hybridize to NHEJ mutated sub-regions and do hybridize to target genomic regions containing an HDR mutation.

In some embodiments, c) comprises determining a concentration of target genomic regions having the NHEJ mutation in the sample by detecting and counting: i) a total number of mixture partitions that do not contain the target genomic region; and ii) a total number of—mixture partitions in which only the target genomic region containing the NHEJ mutation is detected; and—mixture partitions that do not contain the target genomic region, wherein the concentration is calculated as a reciprocal of the average volume of the plurality of mixture partitions multiplied by a negative natural log of a ratio of i) divided by ii).

In some embodiments, c) comprises determining a concentration of target genomic regions having the HDR mutation in the sample by detecting and counting: i) a total number of: —mixture partitions that do not contain the target genomic region; —mixture partitions in which only the target genomic region containing the NHEJ mutation is detected; —mixture partitions in which only the wild-type target genomic region is detected; and—mixture partitions in which only the wild-type target genomic region and the target genomic region containing the NHEJ mutation are detected; and ii) a total number of—i); and—mixture partitions in which the HDR mutation is detected, wherein the concentration is calculated as the reciprocal of an average volume of the plurality of mixture partitions multiplied by a negative natural log of a ratio of i) divided by ii).

In some embodiments, c) comprises determining a concentration of wild-type target genomic regions in the sample by detecting and counting: i) a total number of: —mixture partitions that do not contain the target genomic region; and—mixture partitions in which only the target genomic region containing the NHEJ mutation is detected; and ii) a total number of—i); —mixture partitions in which only the wild-type target genomic region is detected; and—mixture partitions in which only the wild-type target genomic region and the target genomic region containing the NHEJ mutation are detected; and wherein the concentration is calculated as the reciprocal of an average volume of the plurality of mixture partitions multiplied by a negative natural log of a ratio of i) divided by ii).

In another aspect, the present invention provides a method for identifying an optimized condition for genome editing of a cell, the method comprising: a) performing site specific genome editing of a plurality of cells under a first set of conditions to provide first sample of cells; b) performing site specific genome editing of a plurality of cells under a second set of conditions to provide a second sample of cells; c) performing any of the methods described above or elsewhere herein to quantify a number of NHEJ edited target genomic regions and HDR edited target genomic regions in the first and second samples of cells to determine a genome editing efficiency for the first and second set of conditions; d) comparing the genome editing efficiency of the first and second set of conditions to identify a set of conditions that provides a higher genome editing efficiency; and e) selecting the set of conditions that provides higher genome editing efficiency as the optimized condition for genome editing.

In some embodiments, a) comprises contacting the first sample of cells with a first concentration of genome editing reagent; and b) comprises contacting the second sample of cells with a second concentration of genome editing reagent. In some embodiments, a) comprises contacting the first sample of cells with a first genome editing reagent; and b) comprises contacting the second sample of cells with a second structurally different genome editing reagent. In some embodiments, c) comprises determining an HDR genome editing efficiency for the first set of conditions and determining an HDR genome editing efficiency for the second set of conditions; d) comprises comparing the HDR genome editing efficiency of the first and second set of conditions to identify a set of conditions that provides a higher HDR genome editing efficiency; and e) comprises selecting the set of conditions that provides higher HDR genome editing efficiency as the optimized condition for genome editing.

In some cases, c) comprises determining an NHEJ genome editing efficiency for the first set of conditions and determining an NHEJ genome editing efficiency for the second set of conditions; d) comprises comparing the NHEJ genome editing efficiency of the first and second set of conditions to identify a set of conditions that provides a lower NHEJ genome editing efficiency; and e) comprises selecting the set of conditions that provides higher HDR genome editing efficiency and a lower NHEJ genome editing efficiency as the optimized condition for genome editing.

In some embodiments, of one of the foregoing methods, the sample of cells is from a patient to whom genome edited cells have been administered and the method further comprises estimating a number of genome edited cells in the patient from a determined quantity of wild-type target genomic regions, a determined quantity of target genomic regions containing an HDR mutation, and/or a determined quantity of target genomic regions containing an NHEJ mutation.

In one aspect, the present invention provides a method of monitoring a population of cells in a patient, wherein the cells comprise a population of edited genomes (e.g., a clonal population of edited genomes), the method comprising: providing a sample from an individual to whom the cells comprising the population of edited genomes have been administered (e.g., as a component of a treatment); analyzing the sample to determine a number of edited genomes or fragments thereof in the sample; and estimating the number of cells comprising the population of edited genomes (e.g., clonal population of edited genomes) in the patient from the number of edited genomes or fragments thereof in the sample. In some embodiments, the analyzing the sample to determine the number of edited genomes or fragments thereof comprises quantifying homology directed repair (HDR), non-homologous end joining (NHEJ), simultaneous HDR and NHEJ, and/or the number of wild-type (e.g., unedited) genomes or fragments thereof in the sample.

In some cases, the method comprises analyzing the sample to determine the number of edited genomes or fragments thereof by quantifying HDR, NHEJ, or HDR and NHEJ using any one of the foregoing HDR and/or NHEJ quantification methods. In some cases, the analyzing the sample to determine the number of edited genomes or fragments thereof comprises quantifying a number of genomes containing a polymorphism that is induced by genome editing. In some cases, the quantifying comprises droplet digital nucleic acid amplification. In some cases, the analyzing the sample to determine the number of edited genomes or fragments thereof comprises massively parallel sequencing, high throughput sequencing, or single molecule sequencing.

In some cases, one of the foregoing methods further comprises determining whether to administer additional cells comprising the population of edited genomes (e.g., the clonal population of edited genomes) to the patient based on the estimated the number of cells comprising the population of edited genomes in the patient. In some cases, one of the foregoing methods further comprises comparing the estimated number of cells comprising the (e.g., clonal) population of edited genomes in the patient to a number of genome edited cells that have been administered to the patient. In some cases, a difference between the number of cells comprising the (e.g., clonal) population of edited genomes in the patient and the number of cells that have been administered to the patient indicates whether the treatment is or will be successful. In some cases, the method comprises determining a risk factor (e.g., odds ratio) for the success or failure of the treatment based on a change in the number of cells comprising the (e.g., clonal) population of edited genomes in the patient from administration of the cells to obtaining the sample from the patient.

In some cases, if the number of cells comprising the (e.g., clonal) population of edited genomes in the patient from administration of the cells to obtaining the sample from the patient decreases, or substantially decreases (e.g., decreases by at least about 25%, 50%, 75%, 90%, or more), then the method comprises determining to administer additional cells comprising the (e.g., clonal) population of edited genomes to the patient. In some cases a decrease, or substantial decrease (e.g., a decrease of at least about 25%, 50%, 75%, 90%, or more), in the number of cells comprising the (e.g., clonal) population of edited genomes in the patient from administration of the cells to obtaining the sample from the patient indicates that the treatment will not be successful. In some cases, an increase or substantially no decrease in the in the number of cells comprising the (e.g., clonal) population of edited genomes in the patient from administration of the cells to obtaining the sample from the patient indicates that the treatment will be successful. In some cases, a decrease or substantial decrease, in the number of cells comprising the (e.g., clonal) population of edited genomes in the patient from administration of the cells to obtaining the sample from the patient indicates the administration of a drug or chemotherapeutic agent to the patient, or indicates that an adjustment (e.g., a change in dose or a change in the drug administered) in a drug regimen.

In some cases, the method comprises determining whether to administer additional cells comprising the (e.g., clonal) population of edited genomes to the patient based on a change in the number of cells comprising the (e.g., clonal) population of edited genomes in the patient from administration of the cells to obtaining the sample from the patient. In some cases, a decrease in the number of cells comprising the (e.g., clonal) population of edited genomes in the patient from administration of the cells to obtaining the sample from the patient indicates the need to administer additional cells comprising the (e.g., clonal) population of edited genomes to the patient. In some cases, the method comprises determining whether to administer cells comprising a second (e.g., structurally distinct) population (e.g., clonal population) of alternatively edited genomes to the patient based on a change in the number of cells comprising the (e.g., clonal) population of edited genomes in the patient from administration of the cells to obtaining the sample from the patient.

In some embodiments, the method further comprises: analyzing a second sample to estimate a second number of cells comprising the (e.g., clonal) population of edited genomes in the patient, wherein the second sample is a sample that has been taken from the patient at a later point in time than the first sample; and comparing the change in the number of cells comprising the (e.g., clonal) population of edited genomes in the patient from the first to the second sample. In some cases, the change in the number of genome edited cells indicates whether the treatment is or will be successful. In some cases, a decrease (e.g., a substantial decrease of at least 25%, 50%, 75%, 90%, or more) in the number of cells comprising the (e.g., clonal) population of edited genomes in the patient from the first to the second sample indicates that the treatment is or will be unsuccessful. In some cases, an increase (e.g., a substantial increase of at least 25%, 50%, 75%, 90%, or more) in the number of cells comprising the (e.g., clonal) population of edited genomes in the patient from the first to the second sample indicates that the treatment is or will be successful. In some cases a rate of increase or decrease in the number of cells comprising the (e.g., clonal) population of edited genomes in the patient from the first to the second sample indicates that the treatment is or will be successful or unsuccessful respectively.

In some cases, the method comprises determining a risk factor for the success or failure of the treatment based on the change (e.g., increase or decrease) or rate of change in the number of cells comprising the (e.g., clonal) population of edited genomes in the patient from the first to the second sample. In some cases, the risk factor is an odds ratio.

In some embodiments, the method comprises determining whether to administer additional cells comprising the (e.g., clonal) population of edited genomes to the patient based on the change in the number of cells comprising the (e.g., clonal) population of edited genomes in the patient from the first to the second sample. In some cases, a decrease in the number of cells comprising the (e.g., clonal) population of edited genomes in the patient from the first to the second sample indicates the need to administer additional cells comprising the (e.g., clonal) population of edited genomes to the patient. In some cases, the method comprises determining whether to administer cells comprising a second (e.g., structurally distinct) population (e.g., clonal population) of alternatively edited genomes to the patient based on a change in the number of cells comprising the clonal population of edited genomes in the patient from the first to the second sample. For example, a decrease in the number of genome edited cells from the first to the second sample can indicate a need to administer a second population of alternatively edited genomes to the patient.

In another aspect the present invention provides a method of monitoring a population of cells in vitro, wherein the cells comprise a population of edited genomes (e.g., a clonal population of edited genomes), the method comprising: providing a population of cells comprising a population of edited genomes (e.g., clonal population of edited genomes), quantifying a first number of edited genomes in a sample of the population, selecting the population of cells, quantifying a second number of edited genomes in a sample of the population, and comparing the first and second numbers to determine a response to the selection. In some embodiments, the quantifying comprises quantifying homology directed repair (HDR), non-homologous end joining (NHEJ), simultaneous HDR and NHEJ, and/or the number of wild-type (e.g., unedited) genomes or fragments thereof in the sample.

In some cases, the selecting comprises contacting the population of cells with a drug or chemotherapeutic. In some cases, the selecting comprises contacting the population of cells with a growth factor or cytokine. In some cases, the selecting comprises culturing the cells or passaging the cells.

In some cases, the quantifying comprises quantifying HDR, NHEJ, or HDR and NHEJ using any one of the foregoing HDR and/or NHEJ quantification methods. In some cases, the the quantifying comprises quantifying a number of genomes containing a polymorphism that is induced by genome editing. In some cases, the quantifying comprises droplet digital nucleic acid amplification. In some cases, the quantifying comprises massively parallel sequencing, high throughput sequencing, or single molecule sequencing.

In another aspect the present invention provides a method of generating a specified dose of genome edited cells, the method comprising: providing a population of cells comprising a population of edited genomes (e.g., clonal population of edited genomes), quantifying a number of edited genomes in a sample of the population, mixing the population of cells comprising the population of edited genomes with a population of (e.g., wild-type) cells that have not been edited by a site specific genome editing reagent, to obtain a population of cells that has the specified dose of genome edited cells. In some cases, the specified dose of genome edited cells is a dose containing, or containing about, 1%, 10%, 15%, 20%, 25%, 30%, 40%, 50%, 60%, or 75%, genome edited cells. In some cases, the specified dose of genome edited cells is a dose containing, or containing from about, 20% genome edited cells to about 50% genome edited cels.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3 SR); isothermal amplification reactions (e.g., single-primer isothermal amplification (SPIA)); as well as others known to those of skill in the art.

"Amplifying" refers to a step of submitting a solution to conditions sufficient to allow for amplification of a target polynucleotide if all of the components of the reaction are intact. Components of an amplification reaction include, e.g., one or more primers, a polynucleotide template, polymerase, nucleotides, and the like. The term "amplifying" typically refers to an exponential increase in target nucleic acid. However, "amplifying" as used herein can also refer to linear increases in the numbers of a select target sequence of nucleic acid, such as is obtained with cycle sequencing or linear amplification. Amplifying produces an amplification product, or "amplicon."

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled. Primers that prime the amplification (e.g., PCR) of a target polynucleotide sequence are referred to as "amplification primers."

The term "probe" refers to a molecule (e.g., a protein, nucleic acid, aptamer, etc.) that specifically interacts with or specifically binds to, and thus detects, a target polynucleotide. Non-limiting examples of molecules that specifically interact with or specifically bind to a target polynucleotide include nucleic acids (e.g., oligonucleotides), proteins (e.g., antibodies, transcription factors, zinc finger proteins, non-antibody protein scaffolds, etc.), and aptamers. Generally, the probe is labeled with a detectable label. The probe can indicate the presence or level of the target polynucleotide by either an increase or decrease in signal from the detectable label. In some cases, the probes detect the target polynucleotide in an amplification reaction by being digested by the 5' to 3' exonuclease activity of a DNA dependent DNA polymerase.

Exemplary probes include oligonucleotide primers having hairpin structures with a fluorescent molecule held in proximity to a fluorescent quencher until forced apart by primer extension, e.g., Whitecombe et al., Nature Biotechnology, 17: 804-807 (1999)(AMPLIFLUOR™, hairpin primers). Exemplary probes may alternatively comprise an oligonucleotide attached to a fluorophore and a fluorescence quencher, wherein the fluorophore and quencher are in proximity until the oligonucleotide specifically binds to an amplification product, e.g. Gelfand et al., U.S. Pat. No. 5,210,015 (TAQMAN™, PCR probes); Nazarenko et al., Nucleic Acids Research, 25: 2516-2521 (1997)("scorpion probes"); and Tyagi et al., Nature Biotechnology, 16: 49-53 (1998)("molecular beacons"). Such probes may be used to measure the total amount of reaction product at the completion of a reaction or to measure the generation of amplification product during an amplification reaction.

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}$P and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is, or is about, 37, 40, 42, 45, 50, 55, 60, 65, 70, 75, or 80° C.

A "template" refers to a polynucleotide sequence that comprises the polynucleotide sequence to be amplified, flanked by a pair of primer hybridization sites, or adjacent to a primer hybridization site. Thus, a "target template" or "target polynucleotide sequence" comprises the target polynucleotide sequence adjacent to at least one primer hybridization site. In some cases, a "target template" comprises the target polynucleotide sequence flanked by a hybridization site for a "forward" primer and a "reverse" primer.

A "target genomic region" refers to a region of the genome of an organism that is targeted for genome editing by a site-specific genome editing reagent. The target genomic region can be amplified by hybridization and extension of one or more amplification primers. The target genomic region can contain one or more sub-regions that contain a specific targeted cleavage or nick site.

A "site-specific genome editing reagent" refers to a component or set of components that can be used for site-specific genome editing. Generally, such a reagent contains a targeting module and a nuclease or nickase module. Exemplary targeting modules contain nucleic acids, e.g., guide RNAs, such as those utilized in CRISPR/Cas-type systems. Alternatively, the targeting module can be, or be derived from, a transcription factor domain, or a TAL effector DNA binding domain. For example, a zinc-finger domain can be employed as a targeting moiety. Exemplary nuclease or nickase modules include, but are not limited to a type IIS restriction endonuclease (e.g., FokI), a Cas nuclease (e.g., Cas9), or a derivative thereof. In some cases, the site-specific genome editing reagent utilizes a combination of a guide RNA, a "dead" Cas nuclease, and a type IIS restriction endonuclease. Other variations are known in the art.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga maritime*, or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

BRIEF DESCRIPTION OF THE DRAWINGS

FIG. 9B depicts an alignment of two sequences (SEQ ID NOS: 22-24) from an isolated iPS cell clone edited by the genome editing reagent depicted in FIG. 9A. The clone has the C>T HDR mutation in one allele (SEQ ID NO:23) and a 24-bp deletion in the other allele (SEQ ID NO:24). These results indicate that a combination of HDR and NHEJ repair can happen in a single cell, providing compound heterozygous mutant cells.

FIG. 10A-B illustrates a scheme for targeting the RBM20 locus (SEQ ID NOS:25-26 and 28-29) for introduction and detection of an HDR mutation (SEQ ID NOS:30-31). The editing reagents, donor oligonucleotide (SEQ ID NO:27), and a TaqMan based PCR assay detection scheme are depicted in FIG. 10A. Exemplary Cas9, Cas9-nickase, and TALEN genome editing reagents are further depicted in FIG. 10B.

FIG. 11A depicts the basics of the ddPCR assay. FIG. 11B depicts a two-dimensional plot of the resulting ddPCR data for a 1:1 mixture of target genomic regions containing wild-type and HDR alleles. FIG. 11C depicts ddPCR data for a dilution series of the HDR allele in a wild-type background.

FIG. 13C illustrates the quantitative performance of the assay with different ratios of wild-type and mutant target genomic regions. FIG. 13D depicts data from HEK293 cells treated with a Cas9 genome editing reagent, as shown in FIG. 10A. Both HDR+ and NHEJ+ populations were observed in this assay.

DETAILED DESCRIPTION OF THE INVENTION

I. Introduction

Figure 1:
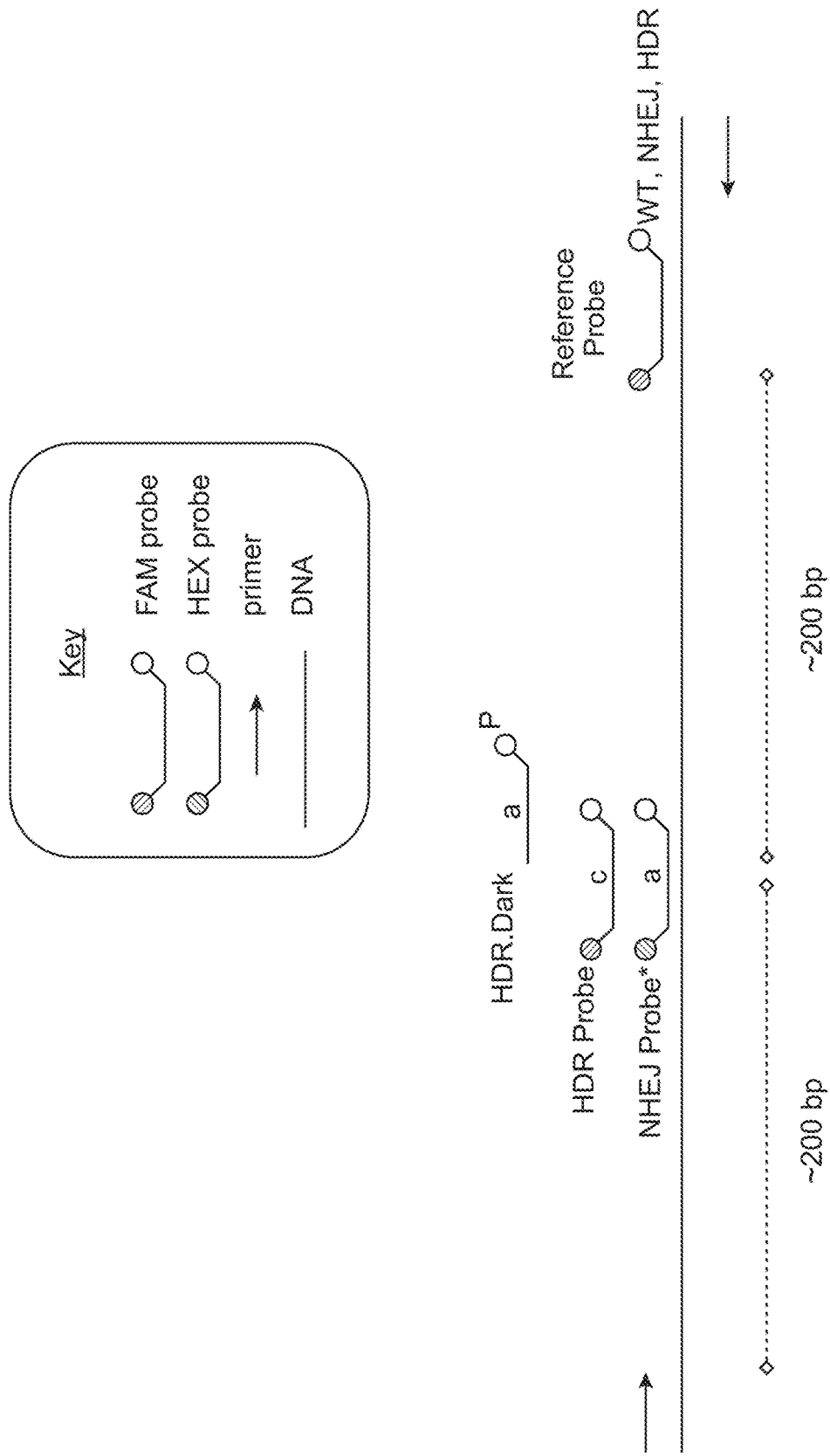
FIG. 1 depicts an exemplary schematic for simultaneous detection of homology dependent repair (HDR) and non-homologous end joining (NHEJ) mutations in a digital amplification (e.g., digital PCR (dPCR)) assay. Forward and reverse amplification primers flank a genomic region targeted by a genome editing reagent. An amplicon (e.g., approximately 100-400 bp in length, or longer) is generated by polymerase chain reaction or other amplification methods. A reference probe hybridizes to, and detects, all amplicon alleles (WT, NHEJ, HDR). An HDR probe detects the HDR edit site. A non-extendible HDR dark probe blocks cross-reactivity to wild-type. An HDR dark probe is not always necessary. An NHEJ drop-off probe hybridizes to the wild-type cut site. NHEJ mutations at the cut site result in loss of hybridization of the NHEJ drop-off probe. In some cases, the NHEJ drop-off probe can hybridize to a region overlapping the target site of the HDR probe and thus block potential HDR cross-reactivity with wild-type template. The position of the NHEJ drop-off probe can vary by cutting strategy; it may lie adjacent to the edit site and not overlap the HDR site at all.

Reagents for site-specific genome editing are becoming increasingly advanced. Generally, such reagents target a genomic region and induce a double stranded cut or two single stranded nicks into the DNA within the target region. Repair of the cutting or nicking can proceed via two alternative pathways. In non-homologous end joining (NHEJ), the cut or nicked ends of a DNA strand are directly ligated without the need for a homologous template nucleic acid. NHEJ can lead to the addition, the deletion, substitution, or a combination thereof, of one or more nucleotides at the repair site. In homology directed repair, the cut or nicked ends of a DNA strand are repaired by polymerization from a homologous template nucleic acid. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid can be introduced to obtain a specific HDR mutation.

Although current genome editing reagents can be quite specific, the introduction of off-target mutations can be a concern. Such off-target mutations can be difficult to identify, as they can occur throughout the genome. Several methods can be used to reduce the frequency of off-target mutations. For example, a low concentration or activity of genome editing reagent can be used to reduce the overall frequency of mutation. By reducing both on-target and off-target mutation frequency, the chances that a single cell will contain both on-target and off-target mutations is reduced. However, this makes it more difficult to identify the desired edited cells in a background population of un-edited cells.

Alternatively, genome editing reagents that require multiple target recognition events can be utilized. For example, a genome editing reagent can be designed that includes a pair of nickases, where each nickase is directed to and nicks DNA at a proximal location within a target genomic region. Off-target activity from individual nickases of the pair is overwhelmingly likely to result in a single nick at the off-target site, which is quickly repaired by the high-fidelity base-excision repair pathway. Such nickase pairs can readily be generated by a variety of methods. For example, a cell can be contacted with a Cas9 nickase mutant, such as the D10A or H840A variants, and a pair of guide RNAs directed to proximal sites within the target genomic region. See, Shen et al., Nat Methods. 2014 April; 11(4):399-402.

As another example, a genome editing reagent containing an obligate heterodimer nuclease can be used to reduce off-target mutations. Such a genome editing reagent can be designed to only generate double stranded breaks when obligate heterodimer nucleases are formed at the target genomic region by site-specific recruitment of each monomer component to an adjacent target half-site. Exemplary obligate heterodimer nucleases include, but are not limited to, those described in U.S. patent application Ser. No. 13/812,857. The targeting function can be provided by a nuclease defective Cas9 (dCas9) and appropriate guide RNAs, a pair of TALENs, or any other nucleic acid sequence specific targeting method.

Despite these and other recent advances in the development of site-specific genome editing reagents, it can be useful to quantify the amount of genome editing achieved in a sample. Such quantification can be useful, in some cases, for optimizing genome editing conditions, or enriching a population of edited cells by sib-selection techniques. For example, genome editing conditions can be optimized to decrease, or increase, the type or amount of NHEJ mutation in comparison to HDR mutation. As another example, genome editing conditions can be optimized to increase the efficiency of editing, thus allowing the use of a low concentration or activity of genome editing reagent without unduly reducing the amount of editing achieved.

Miyaoka et al. Nat Methods. 2014 March; 11(3):291-3, describe a method of quantifying HDR mutations by digital PCR and applying sib-selection to enrich for genome edited cells. This method relies on the use of sequence specific probes for detection of a predetermined mutation introduced by a template nucleic acid during homology directed repair of DNA damage. However, probes for direct detection of NHEJ mutations cannot be so-designed because the type (e.g., insertion or deletion) and extent (e.g., number of base pairs) of the mutation cannot be predicted. In some cases, depending on the genome editing reagent employed, the precise location of the NHEJ mutation also cannot be predicted.

Described herein are methods for quantification of NHEJ mutations. Also described herein are methods for simultaneous quantification of NHEJ and HDR mutations.

II. Methods

Described herein are methods for detecting or quantifying homology directed repair (HDR) genome editing products, non-homologous end joining (NHEJ) genome editing products, or a combination thereof in a sample by digital amplification. Generally the sample is a sample of cells, a sample of genomes extracted from a sample of cells, or fragments thereof. The methods can be used to determine a degree of genome editing achieved for a sample, for identifying optimal conditions for genome editing, or to guide enrichment of populations of cells for genome editing products (e.g., by sib-selection).

The cells, or genomes extracted from cells, can be contacted with a site-specific genome editing reagent under conditions suitable for the genome editing of a target genomic region. In some cases, the cells or genomes are contacted with an HDR template nucleic acid to introduce a pre-determined HDR mutation into the genome. After contact with a site-specific genome editing reagent, the degree of genome editing achieved can be determined using one or more methods described herein. The genome editing reagent can contain one or more nucleases or nickases, or a combination thereof.

A. Detection of NHEJ

In some embodiments, the methods include detecting or quantifying NHEJ genome editing products in a sample. The NHEJ genome editing products can be detected or quantified using a reference probe and an NHEJ drop-off probe. The methods for detecting or quantifying NHEJ genome editing products in a sample can include providing a sample of nucleic acid from the cells or genomes contacted with a genome editing reagent, and forming a reaction mixture containing a reference probe and an NHEJ drop-off probe. The sample can contain NHEJ mutations, HDR mutations, or a combination thereof.

The reaction mixture can be partitioned to form a plurality of mixture partitions having an average volume, the mixture partitions containing: i) a target genomic region; ii) a DNA dependent DNA polymerase; iii) a forward and a reverse oligonucleotide amplification primer, wherein the forward and reverse primers hybridize to opposite strands of, and flank, the target genomic region, and wherein the primers are configured to amplify the target genomic region in the presence of the polymerase; and iv) a detectably labeled oligonucleotide reference probe that hybridizes to the target genomic region, regardless of the allele (i.e., hybridizes to wild-type, HDR, and NHEJ edited target genomic regions).

The mixture partitions can further contain one or more NHEJ drop-off probes.

Generally, the NHEJ drop-off probes are designed to hybridize to a sub-region of the target genomic region containing a cut or nick site targeted by the site-specific genome editing reagent. The design of the one or more NHEJ drop-off probes can vary with the type of genome editing reagent to which the sample has been contacted.

For example, if the genome editing reagent is a Cas9 nuclease and a guide RNA, cut sites are generally 3-5 base pairs directly upstream of a protospacer adjacent motif (PAM). The PAM generally consists of the sequence NGG, although some other PAM sequences can be utilized, such as NGA or NAG. Thus, cut sites can be, for instance, either [5'-20 nt target-NGG-3'] or [5'-CCN-20 nt target-3'], as it is equally efficacious to target the coding or non-coding strand of DNA. When the target site is 5'-20 nt target-NGG, the predicted cut-site is approximately 3-5 base pairs upstream of the 5' end of the NGG PAM. In such cases, the NHEJ drop-off probe can be designed to hybridize to a sub-region containing this predicted cut-site.

As another example, the genome editing reagent can be a pair of guide RNAs targeted to sites adjacent to PAM sequences on opposite strands of the target genomic region, each guide RNA complexed with a nuclease defective, or dead, Cas9 nuclease (dCas9) that is fused to monomer of an obligate heterodimer of a type IIS restriction nuclease (e.g., FokI). In such cases, the cut site is generally from 12 to 21 base pairs between the adjacent PAM sequences on the opposite strands of the targeted genomic region. Thus, the NHEJ drop-off probe can be designed to hybridize to a sub-region containing a predicted cut site from 12 to 21 base pairs between the adjacent PAM sequences. Similar rules can be utilized to design NHEJ drop-off probes for other genome editing reagents.

In some cases, the range of locations of the predicted cut-site can be larger than 12-21 base pairs. In such cases, multiple NHEJ drop off probes can be utilized to cover a larger area of potential NHEJ mutations. Alternatively, the NHEJ drop-off probes can be increased in length; however, in some cases, increasing the length of the drop-off probe can decrease the ability to detect single nucleotide genome edits. In some cases, the genome editing reagent is designed to create multiple cuts or nicks. In such cases, multiple NHEJ drop off probes can be designed to hybridize to the multiple cuts or nicks. For example, the genome editing reagent can be a pair of nickases targeted to nick the target genomic region in proximal locations (e.g., a pair of nick sites separated by less than 1 kb, less than 500 bp, less than 250 bp, less than 200 bp, less than 150 bp, or less than 100 bp) and on opposite strands of the target genomic region. In this example, a pair of NHEJ drop-off probes can be designed to detect NHEJ mutations at each of the nick sites.

The NHEJ-drop off probes can be from 10 to 35 nucleotides in length. In some cases, the NHEJ-drop off probes are 12 to 30 nucleotides, or 18 to 30 nucleotides in length. In some cases, the NHEJ-drop off probes are 12, 13, 14, 15, 16, 17, 18, 19, 20, 21, 22, 23, 24, 25, 26, 27, 28, 29, or 30 nucleotides in length. Generally, the probes are designed to specifically hybridize to the wild-type target sequence but not to hybridize when a mutation is present in the target sequence under the amplification and/or detection conditions of the assay. This specificity of hybridization can be achieved by altering the length of the probe, the GC content, or the amplification and/or detection conditions (e.g., temperature, salt content, etc.).

In some cases, the NHEJ drop-off probe is sensitive to (i.e., detects) both HDR mutations and NHEJ mutations. For example, the genome editing reagent can include an exogenous HDR template nucleic acid. The template nucleic acid can be used as a template to repair a region encompassing, or within, the double strand breaks or paired nicks introduced by the genome editing reagent. Thus, any mutations present in the HDR template nucleic acid relative to the wild-type genome will be introduced. When the HDR site is proximal to, or at, the target cut site, the NHEJ drop-off probe can hybridize to both potential NHEJ edit sites and the potential HDR edit site. In such cases, the NHEJ drop-off probe can detect both HDR mutations and NHEJ mutations by failing to hybridize to target genomic regions containing such mutations.

Moreover, NHEJ mutations and HDR mutations can be distinguished by use of an HDR probe in the reaction mixture. For example, an HDR probe as described herein or an HDR probe as described in Miyaoka et al. 2014. Thus, if the NHEJ drop off probe detects a mutation (HDR or NHEJ), and the HDR probe does not, then the mutation can be classified as NHEJ. Conversely, if the NHEJ probe detects a mutation and the HDR probe also detects a mutation, then the mutation can be classified as HDR. Similarly, in a partition that contains multiple target genomic regions, each with a possible NHEJ and/or HDR mutation, the presence or absence of NHEJ or HDR mutations can be determined by the relative intensity of signal from the different probes. Thus, for example, if a partition contains one target genomic region with an NHEJ mutation and one target genomic region with an HDR mutation, the reference probe signal will indicate multiple target genomic regions, the HDR probe signal will indicate one HDR mutated target genomic region, and the NHEJ drop off probe signal will indicate that the multiple target genomic regions contain a mutation.

The target genomic regions in the plurality of mixture partitions can be amplified by, e.g., subjecting the mixture partitions to PCR amplification conditions. The conditions can include a two or three step thermal cycling protocol. In some cases, a three step thermal cycling protocol is utilized to ensure complete amplification of target genomic regions. For example, in some cases, if a target genomic region, including predicted cut site locations HDR mutation sites (if applicable) and reference probe hybridization sites, is greater than about 200 bp, or greater than about 400 bp, a three step amplification protocol may be selected.

The quantity of empty mixture partitions can be determined by detecting the number of mixture partitions in which the reference probe, or NHEJ drop-off and reference probes, do not detect any target genomic region amplicons. This quantity of empty mixture partitions can be referred to as $N_{neg}$. The quantity of mixture partitions containing only NHEJ edited target genomic region amplicons ($N_{NHEJ}$) in a sample in which an HDR template nucleic acid was not utilized to induce HDR mutations can be determined by detecting the number of mixture partitions in which the reference probe detects target genomic region amplicons, but the NHEJ drop-off probe does not detect any wild-type target genomic region amplicons. The number of mixture partitions containing only NHEJ edited target genomic region amplicons can added to the number of empty mixture partitions to obtain a value referred to as $N_{total}$. The concentration of NHEJ edited genomes in the sample can then be determined by calculating a reciprocal of the average volume of the plurality of mixture partitions multiplied by a negative natural log of the ratio of $N_{neg}$ divided by $N_{total}$.

Similarly, in a reaction mixture in which HDR mutations may be present, HDR and NHEJ drop off probes can be used in combination to determine the quantity of mixture partitions containing only NHEJ edited target genomic region amplicons ($N_{NHEJ}$). For example, the quantity of mixture partitions containing only NHEJ edited target genomic region amplicons ($N_{NHEJ}$) in a sample in which an HDR template nucleic acid was utilized to induce HDR mutations, can be determined by detecting the number of mixture partitions in which the reference probe detects target genomic region amplicons, the NHEJ drop-off probe does not detect any wild-type target genomic region amplicons, and an HDR probe does not detect an HDR allele.

The concentration of wild-type genomes in the sample can be readily derived from the concentration of NHEJ edited genomes in the sample by subtracting the concentration of NHEJ edited genomes from the total concentration of genomes in the NHEJ reaction mixture. Alternatively, the concentration of wild-type genomes can be derived directly by adding together the number of: a) empty mixture partitions ($N_{empty}$); b) mixture partitions containing only NHEJ edited target genomic amplicons ($N_{NHEJ}$); and c) mixture partitions containing at least some detectable wild-type target genomic amplicons ($N_{NHEJ+WT}$ and $N_{WT}$) to obtain $N_{total}$. A value for $N_{neg}$ can be obtained by adding together the number of empty mixture partitions ($N_{empty}$) and mixture partitions containing only NHEJ edited target genomic amplicons ($N_{NHEJ}$). The concentration of wild-type genomes in the sample can then be determined by calculating a reciprocal of the average volume of the plurality of mixture partitions multiplied by a negative natural log of the ratio of $N_{neg}$ divided by $N_{total}$.

B. Detection of NHEJ and HDR in Different Reaction Mixtures

In some embodiments, the methods include detecting or quantifying HDR genome editing products in one reaction mixture and detecting or quantifying NHEJ genome editing products in a different reaction mixture. For example, a sample can be divided into two different reaction mixtures and HDR and NHEJ quantified in the different reaction mixtures (i.e., an HDR reaction mixture and an NHEJ reaction mixture). The NHEJ genome editing products can be detected or quantified using a reference probe and an NHEJ drop-off probe as described above. The HDR genome editing products can be detected or quantified using a reference probe an HDR probe, and optionally an HDR dark probe.

The NHEJ and HDR reaction mixtures can be separately partitioned to form a plurality of mixture partitions having an average volume, the mixture partitions containing: i) a target genomic region; ii) a DNA dependent DNA polymerase; iii) a forward and a reverse oligonucleotide amplification primer, wherein the forward and reverse primers hybridize to opposite strands of, and flank, the target genomic region, and wherein the primers are configured to amplify the target genomic region in the presence of the polymerase; and iv) a detectably labeled oligonucleotide reference probe that hybridizes to the target genomic region, regardless of the allele (i.e., hybridizes to wild-type, HDR, and NHEJ edited target genomic regions).

The mixture partitions generated by partitioning the HDR reaction mixture can further contain one or more HDR probes. Generally, the HDR probes are designed to hybridize to a sub-region of the target genomic region containing an HDR mutation, but not to hybridize to a sub-region that does not contain the HDR mutation. In some cases, the HDR probe can also detect NHEJ mutations. For example, the HDR probe can hybridize to a region overlapping the predicted cut site of the site-specific genome editing reagent, and thus detect the presence or absence of NHEJ induced errors at the repaired cut site. The design of the one or more HDR probes can vary with the number and character of the mutations present on the HDR template nucleic acid.

The HDR probes can be from 10 to 35 nucleotides in length, or longer. In some cases, the HDR probes are 12 to 30 nucleotides, or 18 to 30 nucleotides in length. In some cases, the HDR probes are 12, 13, 14, 15, 16, 17, 18, 19, 20, 21, 22, 23, 24, 25, 26, 27, 28, 29, or 30 nucleotides in length. Generally, the probes are designed to specifically hybridize to the HDR edited target genomic sequence but not to the wild-type target sequence under the amplification and/or detection conditions of the assay. This specificity of hybridization can be achieved by altering the length of the probe, the GC content, or the amplification and/or detection conditions (e.g., temperature, salt content, etc.).

The HDR probe can contain the same detectable label as the reference probe. In such cases, the signal from the HDR probe and the reference probe can be additive, when HDR mutated target genomic regions are detected. Mixture partitions containing both HDR-mutated target genomic regions and non-HDR-mutated target genomic regions (e.g., wild-type) can then be detected as a separate, but possibly overlapping, cluster situated between wild-type only and HDR only target genomic region containing mixture partitions.

The HDR mixture partitions can contain an HDR dark probe. The HDR dark probe can increase the stringency of the assay by decreasing erroneous signal provided by binding of the HDR probe to the wild-type target genomic region. The HDR dark probe is generally designed to compete with the HDR probe for binding to the wild-type target genomic region, but not the HDR mutated target genomic region. In some cases, the HDR dark probe and the HDR probe are the same sequence except at the nucleotides altered by the HDR mutation. Typically, the HDR dark probe is designed to contain a non-extendible 3' end. An exemplary non-extendible 3' end includes, but is not limited to a 3' terminal phosphate. Alternative non-extendible 3' ends include, but are not limited to, those disclosed in, e.g., international patent application publication No. WO 2013/026027.

The target genomic regions in the plurality of HDR mixture partitions can be amplified by, e.g., subjecting the mixture partitions to PCR amplification conditions. The conditions can include a two or three step thermal cycling protocol. In some cases, a three step thermal cycling protocol is utilized to ensure complete amplification of target genomic regions. For example, in some cases, if a target genomic region, including predicted cut site locations, HDR mutation sites, and reference probe hybridization sites, is greater than about 200 bp or 400 bp, a three step amplification protocol may be selected.

NHEJ and wild-type quantification can be performed by analyzing the NHEJ mixture partitions as described above. The concentration of HDR edited genomes can be derived by adding together the number of: a) empty mixture partitions ($N_{empty}$); b) mixture partitions containing only NHEJ edited target genomic amplicons ($N_{NHEJ}$); and c) mixture partitions containing at least some detectable wild-type target genomic amplicons ($N_{NHEJ+WT}$ and $N_{WT}$) to obtain $N_{neg}$. A value for $N_{Total}$ can be obtained by adding $N_{neg}$ and mixture partitions containing at least some detectable HDR edited target genomic amplicons ($N_{HDR}$, $N_{HDR+WT}$, $N_{HDR+NHEJ}$, and $N_{HDR+NHEJ+WT}$). The concentration of wild-type genomes in the sample can then be determined by calculating a reciprocal of the average volume of the plurality of mixture partitions multiplied by a negative natural log of the ratio of $N_{neg}$ divided by $N_{total}$.

C. Simultaneous Detection of NHEJ and HDR

In some embodiments, the methods include simultaneously detecting or quantifying HDR and NHEJ genome editing products in a sample. The HDR and NHEJ genome editing products can be detected or quantified using a reference probe as described herein, one or more NHEJ drop-off probes as described herein, an HDR probe as described herein, and optionally an HDR dark probe as described herein. The methods for detecting or quantifying HDR and NHEJ genome editing products in a sample can include providing a sample of nucleic acid from the cells or genomes contacted with a genome editing reagent, and forming a reaction mixture containing a reference probe, one or more NHEJ drop-off probes, an HDR probe, and optionally an HDR dark probe. In some cases, the simultaneous detection of NHEJ and HDR is performed by forming a single reaction mixture containing a reference probe, one or more NHEJ drop-off probes, an HDR probe, and optionally an HDR dark probe. In some cases, the use of a single reaction mixture can reduce the likelihood of user error or increase the precision or accuracy of the assay.

The reaction mixture can be partitioned to form a plurality of mixture partitions having an average volume, the mixture partitions containing: i) a target genomic region; ii) a DNA dependent DNA polymerase; iii) a forward and a reverse oligonucleotide amplification primer, wherein the forward and reverse primers hybridize to opposite strands of, and flank, the target genomic region, and wherein the primers are configured to amplify the target genomic region in the presence of the polymerase; and iv) a detectably labeled oligonucleotide reference probe that hybridizes to the target genomic region, regardless of the allele (i.e., hybridizes to wild-type, HDR, and NHEJ edited target genomic regions).

The mixture partitions can further contain one or more NHEJ drop-off probes, an HDR probe, and optionally an HDR dark probe. In some cases, one of the one or more NHEJ drop-off probes hybridizes to a sub-region of the target genomic region that overlaps with the hybridization site of the HDR probe. In such cases, the NHEJ probe can substitute for, and render unnecessary, the use of an HDR dark probe.

In some cases, the mixture partitions are formed in single well. In some cases, the use of a single well can reduce the likelihood of user error or increase the precision or accuracy of the assay. For example, a plurality of droplet mixture partitions can be formed in a single well. The mixture partitions in the well can contain: i) a target genomic region; ii) a DNA dependent DNA polymerase; iii) a forward and a reverse oligonucleotide amplification primer, wherein the forward and reverse primers hybridize to opposite strands of, and flank, the target genomic region, and wherein the primers are configured to amplify the target genomic region in the presence of the polymerase; and iv) a detectably labeled oligonucleotide reference probe that hybridizes to the target genomic region, regardless of the allele (i.e., hybridizes to wild-type, HDR, and NHEJ edited target genomic regions). The mixture partitions in the well can further contain one or more NHEJ drop-off probes, an HDR probe, and optionally an HDR dark probe The target genomic regions in the plurality mixture partitions can be amplified by, e.g., subjecting the mixture partitions to PCR amplification conditions. The conditions can include a two or three step thermal cycling protocol. In some cases, a three step thermal cycling protocol is utilized to ensure complete amplification of target genomic regions. For example, in some cases, if a target genomic region, including predicted cut site locations, HDR mutation sites, and reference probe hybridization sites, is greater than about 200 bp, or greater than about 400 bp, a three step amplification protocol may be selected.

NHEJ and wild-type quantification can be performed by analyzing the mixture partitions as described above. The concentration of HDR edited genomes can be derived by adding together the number of: a) empty mixture partitions ($N_{empty}$); b) mixture partitions containing only NHEJ edited target genomic amplicons ($N_{NHEJ}$); and c) mixture partitions containing at least some detectable wild-type target genomic amplicons ($N_{NHEJ+WT}$ and $N_{WT}$) to obtain $N_{neg}$. A value for $N_{Total}$ can be obtained by adding $N_{neg}$ and mixture partitions containing at least some detectable HDR edited target genomic amplicons ($N_{HDR}$, $N_{HDR+WT}$, $N_{HDR+NHEJ}$, and $N_{HDR+NHEJ+WT}$). The concentration of wild-type genomes in the sample can then be determined by calculating a reciprocal of the average volume of the plurality of mixture partitions multiplied by a negative natural log of the ratio of $N_{neg}$ divided by $N_{total}$.

An exemplary schematic for simultaneous detection of HDR and NHEJ is depicted in FIG. 1. As shown in this figure, forward and reverse amplification primers flank a genomic region targeted by a genome editing reagent. An amplicon is generated during multiple rounds of hybridization and extension of the amplification primers by a DNA dependent DNA polymerase (e.g., PCR). The amplicon can be approximately 100-400 bp in length, or longer. Generally, the length of the amplicon is chosen to ensure that there is enough room so that all probes (e.g., reference, NHEJ, and HDR) can bind to their target sequence in the amplicon. In some cases, it is desirable to minimize the size of the amplicon to decrease the amplification time and thereby increase the speed of the assay. In some cases, the size of the amplicon can be determined by the size of the flanking regions upstream and downstream of the target cut or nick site encompassed by the amplification primers. The flanking regions can be approximately 200 bp as depicted in FIG. 1. Alternatively the flanking regions can be approximately 50, 60, 70, 80, 90, 100, 125, 150, 175, 200, 225, 250, or longer. In some cases, the upstream and downstream flanking regions are the same size. In some case, the upstream and downstream flanking regions are different sizes.

As shown in FIG. 1, a reference probe hybridizes to, and detects, all amplicon alleles. An HDR probe detects the HDR edit site. An optional non-extendible HDR dark probe blocks cross-reactivity to wild-type. An NHEJ drop-off probe hybridizes to the wild-type cut site. NHEJ (or HDR) mutations at the cut site result in loss of hybridization of the NHEJ drop-off probe. In some cases, the NHEJ drop-off probe can hybridize to a region overlapping the target site of the HDR probe and thus block potential HDR cross-reactivity with wild-type template, replacing the function of the HDR dark probe. The position of the NHEJ drop-off probe can vary by cutting strategy; it may lie adjacent to the edit site and not overlap the HDR site at all.

Figure 2:
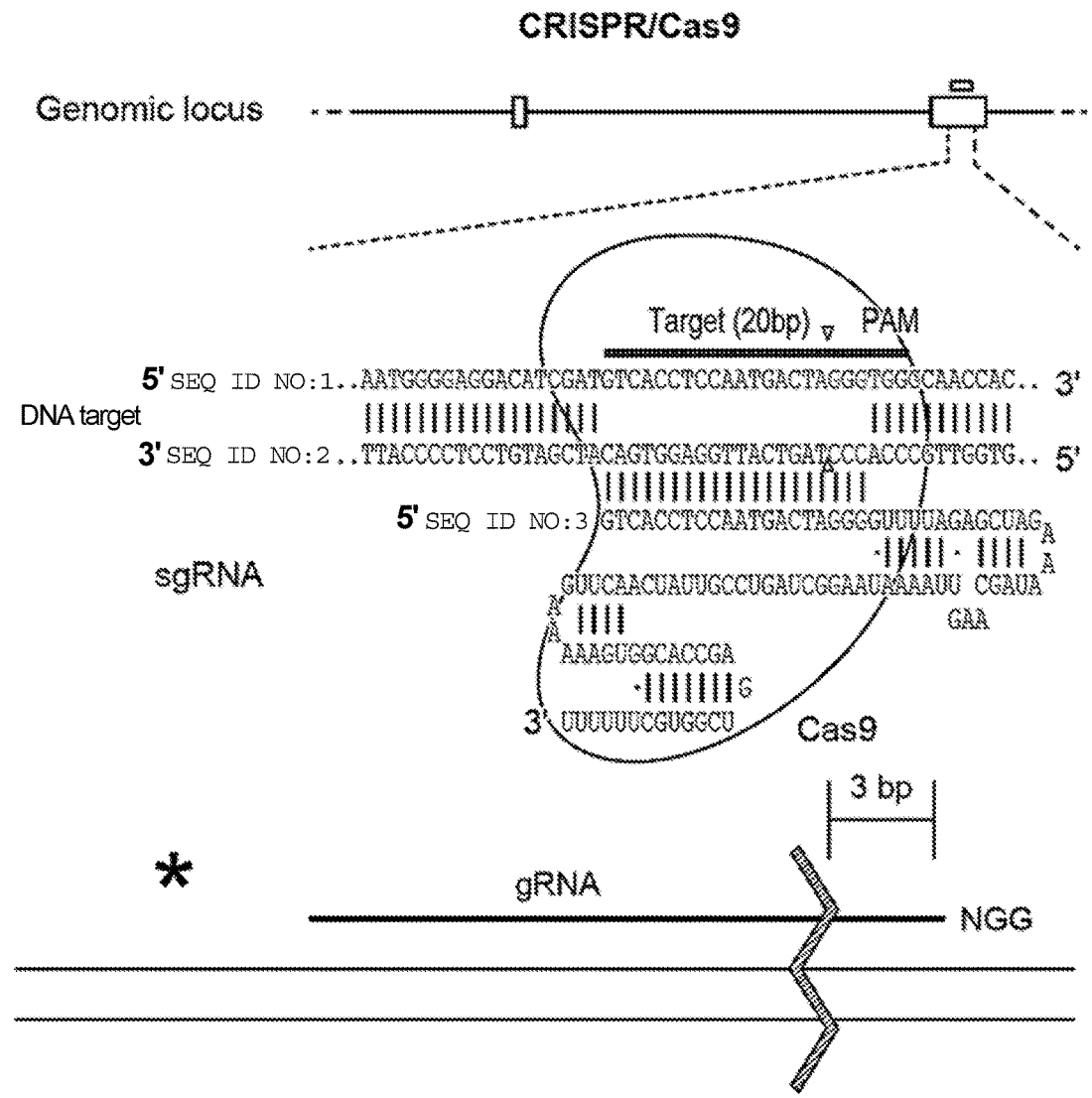
FIG. 2 illustrates how the specific placement of probes for the digital amplification assay can vary based on the specific cutting strategy used. NHEJ drop-off probes can be designed to hybridize to the site of DNA cutting. For example, in CRISPR-Cas9, one double-strand cut is made 3 bp upstream of the PAM site (NGG) where the guide RNA (gRNA) is targeted (SEQ ID NO:3). The NHEJ drop-off probe can be designed to target, and thus interrogate, this cut site. The HDR event might be targeted up to 50-100 bp away. The HDR probe can thus be targeted to hybridize at a certain distance from the NHEJ drop-off probe based on guide and donor sequences used. For Cas9-Nickase, two NHEJ sites are created by using paired gRNAs to cause a single strand break at each gRNA target site (SEQ ID NOS:1-2). In this case, the dPCR assay could contain two NHEJ drop-off probes. This strategy is generalizable to other non-CRISPR cut or nick strategies, like those utilizing Tale effector nucleases or nickases (TALENs) and Zinc-Finger Nucleases or nickases (ZFNs).

An alternative exemplary schematic for simultaneous detection of HDR and NHEJ is depicted in FIG. 2. As shown in this figure, the specific placement of probes for the digital amplification assay can vary based on the specific cutting strategy used. NHEJ drop-off probes can be designed to hybridize to the site of DNA cutting. For example, in CRISPR-Cas9, one double-strand cut is made 3 bp upstream of the PAM site (NGG) where the guide RNA (gRNA) gRNA is targeted. The NHEJ drop-off probe can be designed to target, and thus interrogate, this cut site. The HDR event might be targeted up to 50-100 bp away. The HDR probe can thus be targeted to hybridize at a certain distance from the NHEJ drop-off probe based on guide and donor sequences used.

For Cas9-Nickase, two NHEJ sites are created by using paired gRNAs and a mutant Cas9 that introduces single stranded cuts (nicks) into the target DNA. By targeting two nearby (e.g., within less than about 1 kb, less than about 500 bp, less than about 250 bp, less than about 200 bp, less than about 150 bp, or less than about 100 bp, 75 bp, 50 bp, 25 bp, 15 bp, or 10 bp) sequences with the pair of gRNAs, a pair of proximal single strand nicks is introduced. In this case, the dPCR assay could contain two NHEJ drop-off probes. This strategy is generalizable to other non-CRISPR cut or nick strategies, like those utilizing Tale effector nucleases or nickases (TALENs) and Zinc-Finger Nucleases or nickases (ZFNs).

Figure 3:
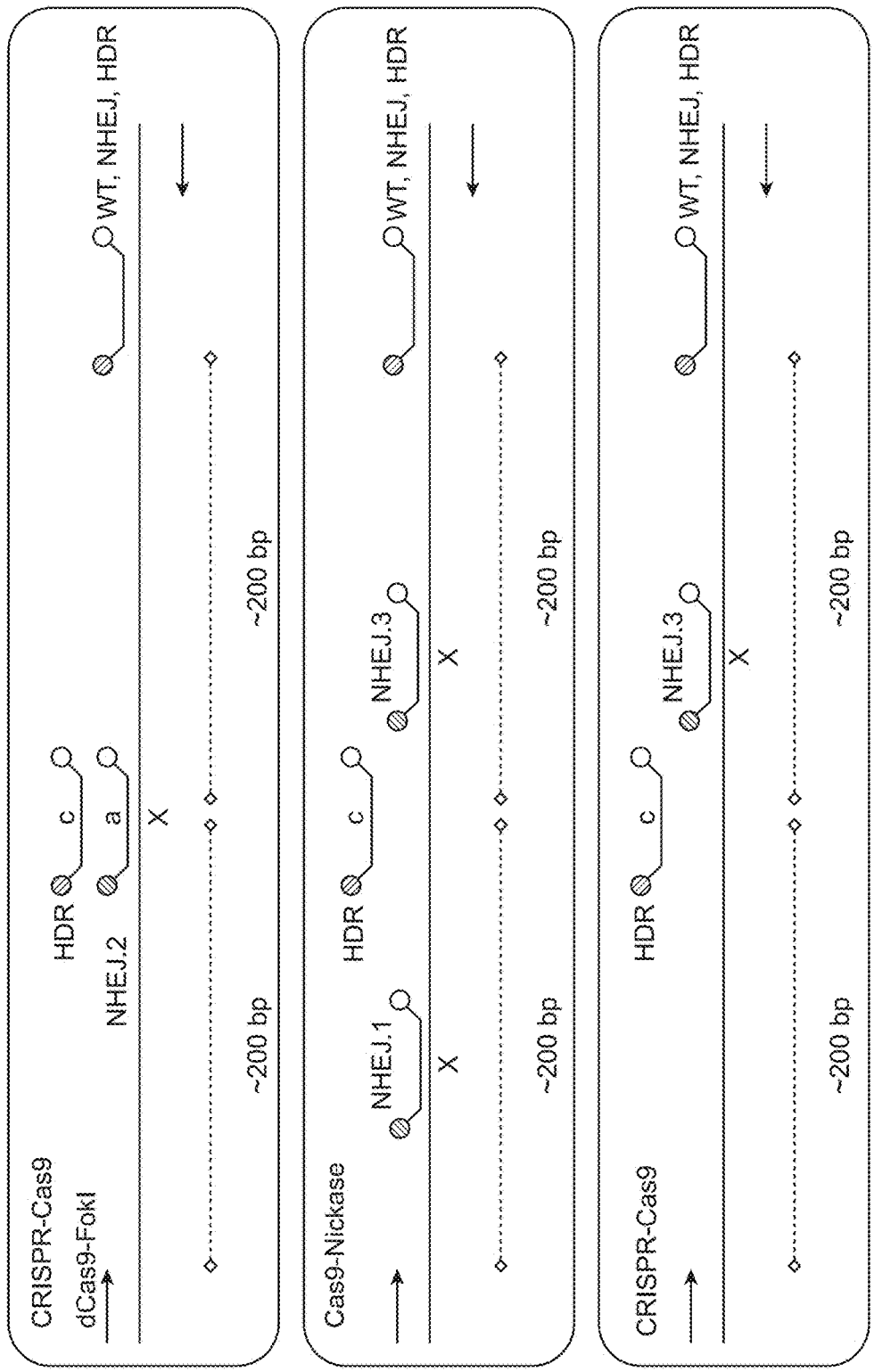
FIG. 3 illustrates several variations on the NHEJ and HDR quantification assay strategy. The choice of assay design can be based on the type of genome editing reagent employed, which determines the type and location of expected HDR and NHEJ modifications. An HDR dark probe (not shown), can also be utilized to increase the stringency of the HDR probe. The genome editing reagent cut-site is depicted by an X, which also corresponds to the location of subsequent NHEJ-induced mutations. This figure illustrates assay design for various CRISPR-Cas9 genome editing strategies, but this approach can be applied to TALENs and ZFNs.

Several alternative exemplary schematics for simultaneous detection of HDR and NHEJ are depicted in FIG. 3. The choice of assay design can be based on the type of genome editing reagent employed, which determines the type and location of expected HDR and NHEJ modifications. An HDR dark probe (not shown), can also be utilized to increase the stringency of the HDR probe. The genome editing reagent cut-site is depicted by an X, which also corresponds to the location of subsequent NHEJ-induced mutations. This figure illustrates assay design for various CRISPR-Cas9 genome editing strategies, but this approach can be applied to TALENs and ZFNs.

Figure 4:
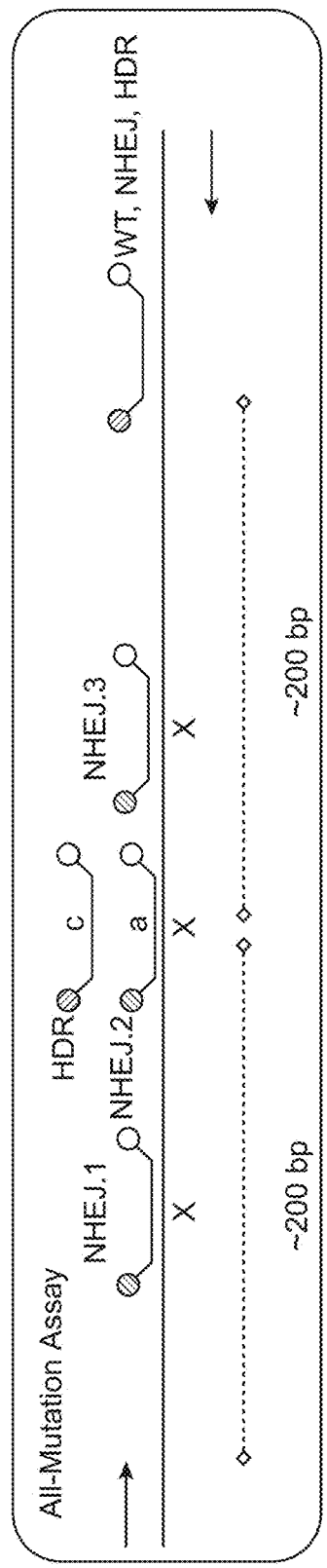
FIG. 4 illustrates an "all-mutation assay" that can be utilized to detect NHEJ and HDR mutations when several different genome editing reagents are employed (e.g., CRISPR/Cas, CRISPR/Cas9-Nickase, dCas9-FokI, etc.). In this example, one primer pair, one reference probe, one HDR probe and one HDR-dark probe (not shown) is used, along with a total of three NHEJ drop-off probes, each one positioned at a given predicted cut site (depicted by an X) as dictated by the three different genome editing reagents. A reduction of signal from any one of the detectably labeled NHEJ drop-off probes indicates an NHEJ event at any of the three possible cut sites generated by the genome editing reagents. Loss of signal from more than one NHEJ drop-off probe due to multiple NHEJ events or one extended event will result in an increase in the magnitude of signal loss.

FIG. 4 illustrates an "all-mutation assay" that can be utilized to detect NHEJ and HDR mutations when several different genome editing reagents are employed (e.g., CRISPR/Cas, CRISPR/Cas9-Nickase, dCas9-FokI, etc.). In this example, one primer pair, one reference probe, one HDR probe and one HDR-dark probe (not shown) is used, along with a total of three NHEJ drop-off probes, each one positioned at a given predicted cut site (depicted by an X) as dictated by the three different genome editing reagents. A reduction of signal from any one of the detectably labeled NHEJ drop-off probes indicates an NHEJ event at any of the three possible cut sites generated by the genome editing reagents. Loss of signal from more than one NHEJ drop-off probe due to multiple NHEJ events or one extended event will result in an increase in the magnitude of signal loss.

Figure 5:
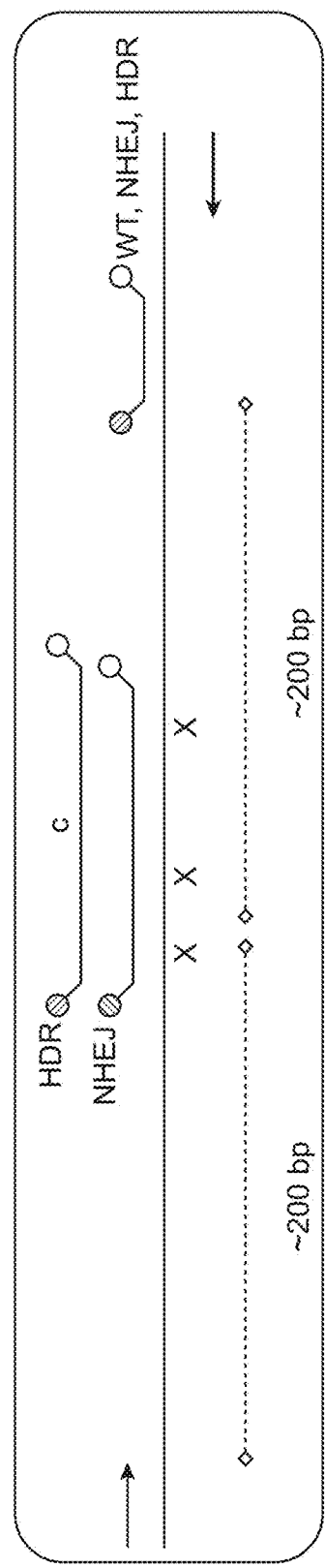
FIG. 5 illustrates an embodiment in which long probes (e.g., greater than 50 bp) are utilized. The NHEJ drop-off probe (which hybridizes to the NHEJ sequence) can detect NHEJ mutations along an extended region of the amplicon. In some cases, the NHEJ drop-off probe can target a site that overlaps the hybridization site of the HDR probe and serve to increase the stringency of the HDR probe. Alternatively, an HDR dark probe can be used (not shown).

FIG. 5 illustrates an embodiment in which long probes (e.g., greater than 50 bp) are utilized. The NHEJ drop-off probe (which hybridizes to the NHEJ sequence) can detect NHEJ mutations along an extended region of the amplicon. In some cases, the NHEJ drop-off probe can target a site that overlaps the hybridization site of the HDR probe and serve to increase the stringency of the HDR probe. Alternatively, an HDR dark probe can be used (not shown).

D. Optimizing Genome Editing

One or more of the methods described herein can be used to for identifying an optimized condition for genome editing of a cell. For example, site-specific genome editing can be performed on a plurality of cells under a first set of conditions to provide first sample of cells; and a second set of conditions to provide a second sample of cells. In some cases, editing is performed under a third, fourth, fifth, sixth, etc. number of conditions. Genomic DNA can be extracted from the cells, and the methods described above utilized to quantify a number of NHEJ edited target genomic regions and/or HDR edited target genomic regions in the different samples of cells to determine a genome editing efficiency for the different conditions. The genome editing efficiency for the different conditions can be compared to identify a set of conditions that provides a higher genome editing efficiency. The higher efficiency can be selected as the optimized condition for genome editing. In some cases, the higher efficiency of HDR editing is identified as the optimized condition for genome editing. In some cases, the higher efficiency of NHEJ editing is identified as the optimized condition for genome editing. In some cases, the higher ratio of the efficiency of NHEJ to HDR editing is identified as the optimized condition for genome editing. In some cases, the higher ratio of the efficiency of HDR to NHEJ editing is identified as the optimized condition for genome editing.

In some cases, the different conditions comprise different concentrations of genome editing reagents. In some cases, the different conditions comprise different types of genome editing reagents. For instance, a zinc-finger nuclease can be compared to a CRISPR/Cas reagent, e.g., with all other variables held constant. In some cases, the different conditions comprise the same or different type of genome editing reagent targeted to different target genomic regions. Thus, for example, the genome editing efficiency targeted to a region of closed chromatin can be compared to the genome editing efficiency targeted to a region of open chromatin.

E. Partitioning

Samples can be partitioned into a plurality of mixture partitions. The use of partitioning can be advantageous to reduce background amplification, reduce amplification bias, increase throughput, provide absolute or relative quantitative detection, or a combination thereof. Partitioning can also allow multiplex detection of different targets (or different mutations in a target). Partitions can include any of a number of types of partitions, including solid partitions (e.g., wells or tubes) or fluid partitions (e.g., aqueous droplets within an oil phase). In some embodiments, the partitions are droplets. In some embodiments, the partitions are micro channels. Methods and compositions for partitioning a sample are described, for example, in published patent applications WO 2010/036352, US 2010/0173394, US 2011/0092373, and US 2011/0092376, the entire content of each of which is incorporated by reference herein.

In some cases, samples are partitioned and detection reagents (e.g., probes, enzyme, etc.) are incorporated into the partitioned samples. In other cases, samples are contacted with detection reagents (e.g., probes, enzyme, etc.) and the sample is then partitioned. In some embodiments, reagents such as probes, primers, buffers, enzymes, substrates, nucleotides, salts, etc. are mixed together prior to partitioning, and then the sample is partitioned. In some cases, the sample is partitioned shortly after mixing reagents together so that substantially all, or the majority, of reactions (e.g., DNA amplification, DNA cleavage, etc.) occur after partitioning. In other cases, the reagents are mixed at a temperature in which reactions proceed slowly, or not at all, the sample is then partitioned, and the reaction temperature is adjusted to allow the reaction to proceed. For example, the reagents can be combined on ice, at less than 5° C., or at 0, 1, 2, 3, 4, 5, 6, 7, 8, 9, 10, 11, 12, 13, 14, 15, 16, 17, 18, 19, 20, 20-25, 25-30, or 30-35° C. or more. In general, one of skill in the art will know how to select a temperature at which the one or more reactions are inhibited. In some cases, a combination of temperature and time are utilized to avoid substantial reaction prior to partitioning.

Additionally, reagents and sample can be mixed using one or more hot start enzymes, such as a hot start DNA-Dependent DNA polymerase. Thus, sample and one or more of buffers, salts, nucleotides, probes, labels, enzymes, etc. can be mixed and then partitioned. Subsequently, the reaction catalyzed by the hot start enzyme, can be initiated by heating the mixture partitions to activate the one or more hot-start enzymes.

Additionally, sample and reagents (e.g., one or more of buffers, salts, nucleotides, probes, labels, enzymes, etc.) can be mixed together without one or more reagents necessary to initiate an intended reaction (e.g., DNA amplification). The mixture can then be partitioned into a set of first partition mixtures and then the one or more essential reagents can be provided by fusing the set of first partition mixtures with a set of second partition mixtures that provide the essential reagent. Alternatively, the essential reagent can be added to the first partition mixtures without forming second partition mixtures. For example, the essential reagent can diffuse into the set of first partition mixture water-in-oil droplets. As another example, the missing reagent can be directed to a set of micro channels which contain the set of first partition mixtures.

In some embodiments, the sample is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplet is formed by flowing an oil phase through an aqueous sample comprising identification signatures to be detected. In some embodiments, the aqueous sample comprising the identification signatures to be detected further comprises a buffered solution and two or more probes for detecting the identification signatures.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or not. The microcapsules can be resistant to coalescence and/or flocculation across a wide range of thermal and mechanical processing.

Following conversion, the microcapsules can be stored at about 70°, −20°, 0°, 3°, 4°, 5°, 6°, 7°, 8°, 9°, 10°, 15°, 20°, 25°, 30°, 35°, or 40° C. In some embodiments these capsules are useful for storage or transport of partition mixtures. For example, a sample can be collected at one location, partitioned into droplets containing enzymes, buffers, probes, and/or primers, optionally one or more amplification reactions can be performed, the partitions can then be heated to perform microencapsulation, and the microcapsules can be stored or transported for further analysis.

The microcapsule partitions can contain one or more probes (e.g., labeled probes as described herein) and can resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions can be incubated per mL. In some embodiments, the sample-probe incubations occur in a single well, e.g., a well of a microtiter plate, without inter-mixing between partitions. The microcapsules can also contain other components necessary for the incubation.

In some embodiments, the sample is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the sample is partitioned into a sufficient number of partitions such that at least a majority of partitions have no more than 1-5 target genomic regions (e.g., no more than about 0.5, 1, 2, 3, 4, or 5 target genomic regions). In some embodiments, on average about 0.5, 1, 2, 3, 4, or 5 target genomic regions are present in each partition. In some embodiments, on average about 0.001, 0.005, 0.01, 0.05, 0.1, 0.5, 1, 2, 3, 4, or 5 target genomic regions are present in each partition. In some embodiments, at least one partition contains no target genomic regions (the partition is "empty"). In some embodiments, at least about 1%, 2%, 3%, 4%, 5%, 6%, 7%, 8%, 9%, or 10% of the partitions contain no target genomic regions. Generally, partitions can contain an excess of enzyme, probes, and primers such that each mixture partition is likely to successfully amplify any target genomic regions present in the partition.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

F. Monitoring of Genome Edited Cells

The future of gene editing may require monitoring of the gene edits that have been made in the populations of genome edited cells. The monitoring can be performed on a population of genome edited therapeutic cells that are transfused into patients (humans or animals). The monitoring can be performed on a population of genome edited cells that are cultured, passaged, and/or selected in vitro to assess efficacy of an indicated treatment. The cells may pluripotent (e.g., induced pluripotent), multipotent, or unipotent stem cells, such as hematopoietic stem cells. Alternatively, the cells can be somatic cells or terminally differentiated cells derived from stem cells (e.g., terminally differentiated induced pluripotent stem cells).

The monitoring can be used to detect or infer the presence or absence of a genome edit. In some cases, the monitoring is quantitative, relatively quantitative, or provides absolute quantitation. The monitoring can be done using partitioning based assays, such as assays that utilize digital amplification. The monitoring can be done using droplet digital assays, such as ddPCR assays. Droplet digital assays for mutation detection include, e.g., those described in U.S. 2014/0309128. In some cases, the monitoring is done using detection of an inserted HDR template during homology directed repair of a site-specific genome editing reagent cleavage or nick pair site. In some cases, the monitoring is performed by simultaneous quantification of HDR and NHEJ mutations in a sample containing a population of cells that have been contacted with a genome editing reagent or a genome editing reagent and an HDR template oligonucleotide. In some cases, the monitoring is performed by massively parallel sequencing, such as targeted or whole genome massively parallel sequencing.

The testing can be done using tissue, blood, whole blood (or a fraction thereof), plasma, serum, urine, saliva, fecal matter, or any other fluid or substance that can be extracted from a human or animal. The testing can include monitoring of specific tissue types to determine if a genome edited cell transfusion has been successful, a percentage of cells from the tissue that contain the genome edit, presence or absence of the genome edit in the sample, or a change or rate of change in the relative or absolute abundance of the genome edit (or cells containing the genome edit) in the sample.

In some cases, a threshold (e.g., a percentage based threshold) may correlate with therapeutic outcomes. For example, a percentage of genome edited cells in a sample over or under a threshold may indicate or predict success of the treatment or guide treatment decisions. In some cases, non-threshold methods such as linear or logarithmic correlation between the number of genome edited cells in a sample and therapeutic outcome may be obtained or calculated, e.g., to indicate or predict success of a treatment, monitor treatment progress, or to guide treatment decisions. Determination of a risk factor for the successful or unsuccessful treatment with the genome edited cells can be performed. The risk factor can be determined using statistical techniques (i.e. determination of odds ratios). In some cases, the presence or absence of the genome edited cells in the sample can be correlated with therapeutic outcomes or diagnosis or detection of various disease states that are associated with particular tissue types and with the intent of guiding treatment decisions.

Also described herein are methods of providing reports or other information to physicians or medical centers of the presence, absence, or quantity of genome edited cells or edited genomes in a sample. The information can be used to guide therapeutic decisions, e.g., the information can be used to guide whether there is a need to administer more edited cells, or whether a different edit may be necessary. The information or report can be based on the testing results, meeting of thresholds, or correlative risk factors.

In some embodiments, a database can be compiled or populated that can collect and/or store the information (e.g., therapeutic outcomes) of many patients' genome editing testing or treatment results. In some cases, the information can be correlated with treatment decisions, such as administration of additional or alternative genome edited cells or other treatments known in the art (e.g., chemotherapy, such as anti-cancer antibody or antibody drug conjugate therapy).

In some embodiments, a population of genome edited cells can be obtained (e.g., by use of CRISPR/Cas, TALENS, zinc finger nucleases, or other methods) or provided, the population can be administered to a patient, and then a sample can be obtained from the patient and analyzed to infer the number of genome edited cells in the patient. In some cases, the number of genome edited cells in the patient is compared to a number of genome edited cells administered to the patient. In some cases, the number of genome edited cells in the patient is compared to a previously determined number of genome edited cells in the patient inferred from a previously obtained sample. In some cases, the number of genome edited cells in the patient is compared to a subsequently determined number of genome edited cells in the patient inferred from a subsequently obtained sample. An increase or substantial increase in the number of genome edited cells in the patient, or a lack of a decrease or substantial decrease in the number of genome edited cells in the patient can indicate treatment success or a likelihood of successful treatment. A decrease or substantial decrease or a lack of increase or substantial increase in the number of genome edited cells in the patient can indicate treatment failure or a likelihood of treatment failure. Alternatively, such a decrease or lack of increase can indicate administration of additional genome edited cells or a change in a treatment (e.g., drug) regimen. In some cases, the rate of increase or decrease indicates treatment success or failure or indicates a need to administer additional genome edited cells. In some cases, one of the foregoing methods described herein can further include administering additional or alternative genome edited cells to a subject in need thereof, administering cells to a subject in need thereof that comprise a different genome edit than previously administered genome edited cells, or administering a change in a treatment regimen (e.g., a change in drug or dose) to a subject in need thereof.

In some embodiments, a population of genome edited cells can be obtained (e.g., by use of CRISPR/Cas, TALENS, zinc finger nucleases, or other methods) or provided, the population can be quantified to determine a number of genome edited cells in the population or the number can be determined from a database or other information repository. The population can then be selected in vitro and the effect of the selection can be determined by quantifying a number of genome edited cells in the population after selection. The selection can comprise in vitro culture, in vitro cell culture passaging, or contacting the cells in vitro with a drug or chemotherapeutic.

An increase or substantial increase in the number of genome edited cells after selection, or a lack of a decrease or substantial decrease in the number of genome edited cells after selection can indicate treatment success or a likelihood of successful treatment if the cells are administered to a subject in need thereof. A decrease or substantial decrease or a lack of increase or substantial increase in the number of genome edited cells in the patient can indicate treatment failure or a likelihood of treatment failure if the cells are administered to a subject in need thereof. Alternatively, such a decrease or lack of increase can indicate administration of additional genome edited cells or a change in a treatment regimen (e.g., a change in drug or dose) if the cells are administered to a subject in need thereof. In some cases, the rate of increase or decrease indicates treatment success or failure, indicates a need to administer additional genome edited cells, or indicates a change in a treatment regimen (e.g., a change in drug or dose) if the cells are administered to a subject in need thereof. In some cases, one of the foregoing methods described herein can further include administering genome edited cells to a subject in need thereof, administering cells to a subject in need thereof that comprise a different genome edit than the in vitro selected cells, or administering a change in a treatment regimen (e.g., a change in drug or dose) to a subject in need thereof.

II. Reaction Mixtures

Described herein is a reaction mixture containing i) a target genomic region; ii) a DNA dependent DNA polymerase; iii) a forward and a reverse oligonucleotide amplification primer, wherein the forward and reverse primers hybridize to opposite strands of, and flank, the target genomic region, and wherein the primers are configured to amplify the target genomic region in the presence of the polymerase; iv) a detectably labeled oligonucleotide reference probe that hybridizes to the target genomic region, regardless of the allele (i.e., hybridizes to wild-type, HDR, and NHEJ edited target genomic regions); v) one or more NHEJ drop-off probes; vi) an HDR probe; and optionally vii) an HDR dark probe. In some cases, one of the one or more NHEJ drop-off probes hybridizes to a sub-region of the target genomic region that overlaps with the hybridization site of the HDR probe. In such cases, the NHEJ probe can substitute for, and render unnecessary, the use of an HDR dark probe.

In some cases, the reaction mixture is a reaction mixture in a partition having a volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some cases, the reaction mixture is in a partition having a diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some cases, the reaction mixture is in a partition having a diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns.

Also described herein are sets of such reaction mixtures. The set can contain at least 500 reaction mixtures, at least 1000 reaction mixtures, at least 2000 reaction mixtures, at least 3000 reaction mixtures, at least 4000 reaction mixtures, at least 5000 reaction mixtures, at least 6000 reaction mixtures, at least 7000 reaction mixtures, at least 8000 reaction mixtures, at least 10,000 reaction mixtures, at least 15,000 reaction mixtures, at least 20,000 reaction mixtures, at least 30,000 reaction mixtures, at least 40,000 reaction mixtures, at least 50,000 reaction mixtures, at least 60,000 reaction mixtures, at least 70,000 reaction mixtures, at least 80,000 reaction mixtures, at least 90,000 reaction mixtures, at least 100,000 reaction mixtures, at least 200,000 reaction mixtures, at least 300,000 reaction mixtures, at least 400,000 reaction mixtures, at least 500,000 reaction mixtures, at least 600,000 reaction mixtures, at least 700,000 reaction mixtures, at least 800,000 reaction mixtures, at least 900,000 reaction mixtures, at least 1,000,000 reaction mixtures, at least 2,000,000 reaction mixtures, at least 3,000,000 reaction mixtures, at least 4,000,000 reaction mixtures, at least 5,000,000 reaction mixtures, at least 10,000,000 reaction mixtures, at least 20,000,000 reaction mixtures, at least 30,000,000 reaction mixtures, at least 40,000,000 reaction mixtures, at least 50,000,000 reaction mixtures, at least 60,000,000 reaction mixtures, at least 70,000,000 reaction mixtures, at least 80,000,000 reaction mixtures, at least 90,000,000 reaction mixtures, at least 100,000,000 reaction mixtures, at least 150,000,000 reaction mixtures, or at least 200,000,000 reaction mixtures.

In some cases, on average about 0.001, 0.005, 0.01, 0.05, 0.1, 0.5, 1, 2, 3, 4, or 5 target genomic regions are present in each reaction mixture of the set of reaction mixtures. In some embodiments, at least one reaction mixture of the set of reaction mixtures contains no target genomic regions. In some embodiments, at least about 1%, 2%, 3%, 4%, 5%, 6%, 7%, 8%, 9%, or 10% of the reaction mixtures of the set of reaction mixtures contain no target genomic regions.

All patents, patent applications, and other publications, including GenBank Accession Numbers, cited in this application are incorporated by reference in the entirety for all purposes.

EXAMPLES

The following examples are provided by way of illustration only and not by way of limitation. Those of skill in the art will readily recognize a variety of non-critical parameters that could be changed or modified to yield essentially the same or similar results.

Example 1: Use of Digital PCR for Simultaneous Quantification of HDR and NHEJ Events in Genome-Edited Cells Materials and Methods Primers:

Forward (F) and reverse (R) primers are designed to generate an amplicon of ~200-400 bp around the targeted edit site (HDR). The edit site should sit roughly in the middle of this amplicon (~100-200 bp of sequence 5' and 3' of the intended edit site). Amplification primers designed to generate shorter or longer amplicons can also be utilized if desired.

Probes:

Reference Probe: a fluorescently-labeled reference probe (e.g., FAM) hybridizes upstream and adjacent to the reverse amplification primer, or downstream and adjacent to the forward amplification primer. This reference probe can be used to detect and count all mixture partitions containing amplicons, regardless of allele (WT, NHEJ, or HDR). For maximal signal, the reference probe should be on the same strand as the amplification primer to which it is adjacent. However, the reference probe can be designed to hybridize to either strand of the amplicon.

HDR Probe: a second fluorescently-labeled probe is designed to hybridize to a genomic region overlapping the HDR edit site. The HDR and reference probes can be labeled with the same fluorescent label, or with different fluorescent labels.

HDR Dark Probe: a second "dark" oligo probe, which includes a non-extendible 3' end and no fluorophore label, is designed that is nearly identical in sequence to the HDR probe, except for the HDR edited position. In the Dark Probe, this position complements the wild-type (non-edited) sequence. The purpose of this probe is to minimize cross-reactivity of the HDR Probe with wild-type DNA. This improves separation between WT and HDR cluster groups in the 2D plot. In some assay designs, a HDR dark probe may not be necessary at all. In some cases, an NHEJ drop-off probe that directly competes with the HDR probe for binding to a wild-type sequence can compensate for the lack of an HDR dark probe.

NHEJ Drop-off Probe: The NHEJ drop-off probe indicates a mutation (NHEJ) event when probe signal is lost, not gained. It is a negative signal. The probe is designed to hybridize to a wild-type sequence at the site where DNA is targeted for cutting by the specific cutting system (e.g., CRISPR-Cas9 cuts 3-5 bases 5' upstream of the PAM NGG site. When that wild-type sequence is mutated, for example by an indel caused by NHEJ, the probe "drops off" and cannot bind; therefore, loss of fluorescence amplitude (e.g., HEX if the NHEJ drop-off probe is labeled with HEX) is indicative of an NHEJ event (with only the FAM reference signal remaining to mark this allele). In the case of genome editing strategies with more than one cut site (e.g., Cas9-Nickase), more than one NHEJ drop-off probe can be required to assay all potential NHEJ mutation sites. Alternatively, a longer NHEJ drop-off probe can be utilized to hybridize to (and thus interrogate) multiple potential NHEJ sites.

Figure 6:
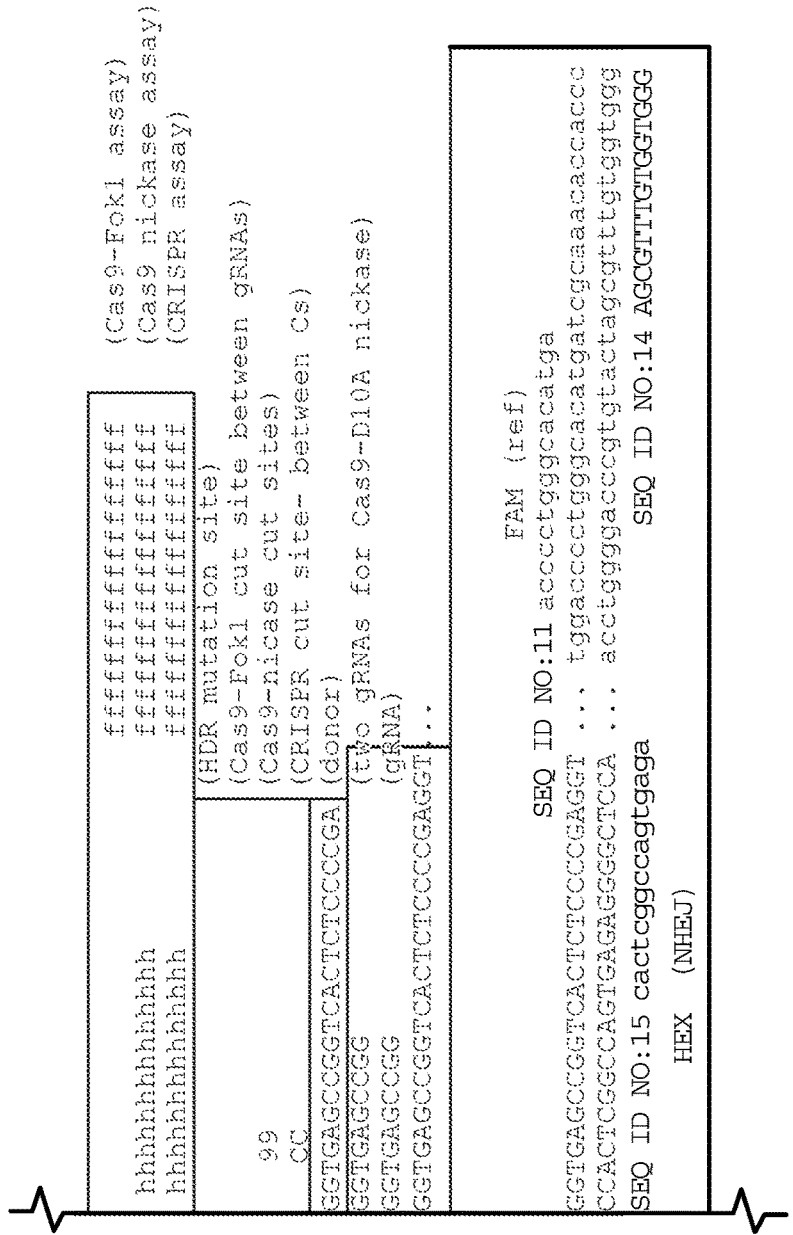
FIG. 6 illustrates an example assay design to quantify NHEJ (SEQ ID NOS:9, 15 and 16) and HDR (SEQ ID NO:10) mutations at the genomic site RBM20 R636S (SEQ IDS NOS:12-13) with three different genome editing reagents (CRISPR-Cas9, Cas9-Nickase, and dCas9-FokI).

Exemplary probe and primer compositions for quantifying NHEJ (SEQ ID NOS:9, 15 and 16) and HDR (SEQ ID NO:10) mutations at the genomic site RBM20 R636S (SEQ IDS NOS:12-13) with three different genome editing reagents (CRISPR-Cas9, Cas9-Nickase, and dCas9-FokI) are illustrated in FIG. 6.

Assay composition: a reaction mixture is formed at a final 1× concentration containing the following:
  Forward and Reverse amplification primers: each at 900 nM (SEQ ID NOS:8 and 14)
  Reference Probe: 250 nM (SEQ ID NO:11)
  HDR Probe: 250 nM
  HDR dark probe: 500 nM
  NHEJ Drop-off Probe (s): 250 nM each
Digital PCR Reaction Setup:
  The digital PCR assay is set up using standard protocols known in the art. For example, 100 ng of genomic DNA sample (30,000 human genome equivalents) are combined with supermix (ddPCR Supermix for Probes (no dUTP)), assay buffer, 2 U of a restriction endonuclease that does not cut the wild-type or HDR edited amplicon (e.g., a six-cutter (or longer) like HindIII-HF) and water. The components are thoroughly mixed (e.g., by vortexing). Partitioning is performed (e.g., droplets are generated) and the partitions are thermal cycled.
Thermal cycling protocol: to accommodate long amplicons, a 3-step thermal cycling protocol can be used. In some cases, a 2 step protocol is adequate. A 3-step protocol with a 2 minute extension should adequately cover amplicons up to 1 kB. Amplicons are generated according to the following exemplary protocol:
  95° C., 10 min
  94° C. 30 sec
  Anneal Temp (as defined by Temp Gradient), e.g., 59° C., 1 min
  72° C., 2 min
  Go to step 2, 39×
  98° C., 10 min
  12° C., hold
  Detect hybridization of fluorescently-labeled probes in the partitions Using this method with droplet digital PCR (ddPCR), the maximal number of NHEJ mutant copies will be read when 0.6 to 1.6 copies per droplet (cpd) of genomic DNA is loaded per well. This represents ~40 ng-100 ng of human genomic DNA per well. 1 cpd loading (66 ng) is optimal mathematically, but real-world factors like sample integrity and assay performance will also influence performance at 1 cpd loading. For example, at higher loading, separation between signals from droplets containing wild-type target genomic region and HDR-edited target genomic region can be reduced. Generally, 100 ng of genomic DNA/well is an amount that will provide robust and accurate quantification by ddPCR, but running a sample dilution series using appropriate controls like gblocks can identify the optimal loading for a given assay.

Analysis:

Cluster groups are first identified. For example, cluster groups can be identified in Quantasoft by lasso thresholding. When two channel detection is utilized, and the HDR and reference probes are labeled with the same fluorescent label (e.g., FAM), the fluorescent signal in partitions containing HDR-edited target genomic regions is an additive function of the signal from both the HDR and the reference probes.

Figure 7:
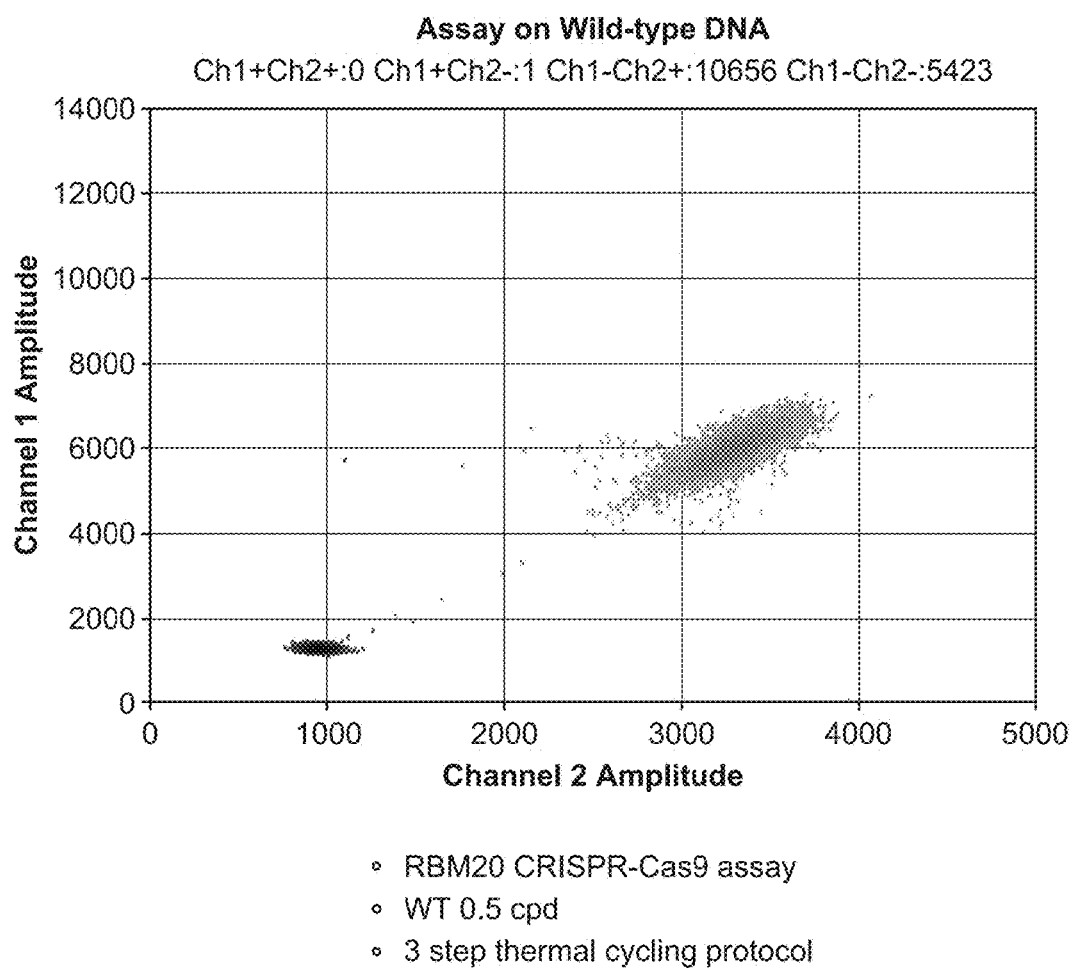
FIG. 7 illustrates data resulting from a simulated assay depicted in FIG. 6 with a CRISPR-Cas9 genome editing reagent. The results are generated using wild-type only genomic DNA as input.

To correctly lasso the given clusters, the positive control wells can be used to identify correct cluster positions and amplitudes. An example positive control well contains wild-type (WT) DNA at same loading regimen as the samples, plus gblock synthetic template controls at a given percent (e.g., 5% mutant copies). Another example positive control is a well that contains only WT DNA (FIG. 7). One can thus use the control well cluster positions to assign clusters in the sample wells.

Figure 8:
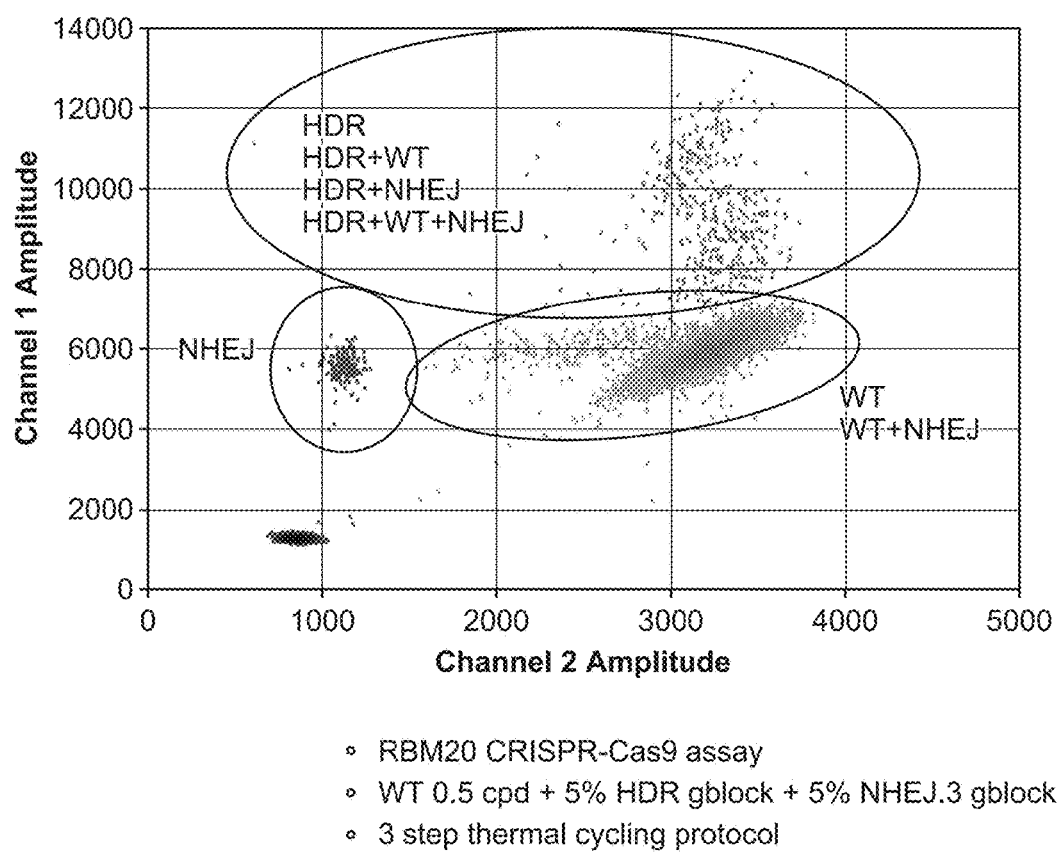
FIG. 8 illustrates data resulting from a simulated assay depicted in FIG. 6 with a CRISPR-Cas9 genome editing reagent. The results are generated by doping a sample of wild-type template at a concentration of 0.5 copies per droplet with 5% simulated HDR and 5% simulated NHEJ template. The data can be analyzed to determine the concentration of edited genomes in a sample. Such data can be used to determine the HDR, NHEJ, or both HDR and NHEJ genome editing efficiency of a genome editing reagent or protocol.

Using the described assay strategy, the cluster classes will appear and can be lasso thresholded in this manner:
  Ch1+Ch2+ droplets: WT+WT/NHEJ droplets
  Ch1+Ch2−: NHEJ
  Ch1++Ch2+: HDR+HDR/WT droplets
  Ch1−Ch2−: negatives Note in this example, a given cluster might contain more than one droplet group (as indicated by oval overlays, approximately (see FIG. 8)). The analysis method takes this fact into account when computing a concentration call for a given species, such as NHEJ alleles. This enables accurate quantification even at higher loading regimens.

The concentration calls (copies/μl) of HDR, NHEJ, and wild-type alleles can be determined per well, including with 95% confidence intervals. From these numbers, percent NHEJ and percent HDR as well as ratio HDR:NHEJ per sample per well can be easily derived.

Quantification:

The standard formula for ddPCR quantification is:

$$c = -\ln\left(\frac{N_{neg}}{N_{total}}\right) / V_{droplet}$$

where
$N_{neg}$=the number of droplets that do not contain the species of interest
$N_{total}$=the total number of droplets For the assay described here, some of the droplet populations cannot easily be separated (e.g., the wild-type (WT) and NHEJ+WT populations). To quantify in this case, an appropriate subset of droplets is used to calculate $N_{neg}$ and $N_{total}$.

Definitions:

$N_{empty}$=the number of droplets in the cluster labeled "empty" (black)

$N_{NHEJ}$=the number of droplets in the cluster labeled "NHEJ" (blue)

$N_{WT+}$=the total number of droplets in the clusters labeled "WT" and "NHEJ+WT" (green)

$N_{HDR+}$=the total number of droplets in the clusters labeled "HDR" and "HDR+WT" (orange) plus the number of droplets in the clusters "HDR+NHEJ" and "HDR+NHEJ+WT" (too few droplets to be seen clearly in data)

N=the total number of observed droplets

For NHEJ quantification:

$N_{total}=N_{empty}+N_{NHEJ}$
$N_{neg}=N_{empty}$

For HDR quantification:

$N_{total}=N_{empty}+N_{NHEJ}+N_{WT+}+N_{HDR+}$
$N_{neg}=N_{empty}+N_{NHEJ}+N_{WT+}$ For WT quantification:

$N_{total}=N_{empty}+N_{NHEJ}+N_{WT+}$
$N_{neg}=N_{empty}+N_{NHEJ}$

Example 2: Simultaneous Quantification of HDR and NHEJ Events Induced by Sequence—Specific Nucleases Using ddPCR Introduction Sequence-specific nucleases such as TALENs and the CRISPR/Cas9 system activate the DNA repair pathways of non-homologous end joining (NHEJ) or homology-directed repair (HDR) at target sites. Although error-prone, NHEJ is useful for disrupting gene function. For many applications HDR is more desirable than NHEJ, since HDR utilizes homologous donor DNA to produce precise gene repair. Since NHEJ and HDR involve different repair enzymes, it is conceivable that conditions could be achieved with high HDR and low NHEJ. However, methods for altering the balance between NHEJ and HDR are elusive, since we lack a rapid sensitive assay to quantify NHEJ and HDR at endogenous genomic loci. To overcome this hurdle, a method is described herein to detect NHEJ and HDR simultaneously based on droplet digital PCR (ddPCR) and fluorescent oligonucleotide probes specific to wild-type (WT), NHEJ, and HDR alleles. The method can allow testing of multiple conditions for genome editing including different types of sequence-specific nucleases and donor DNAs in order to tilt the balance between NHEJ and HDR towards the desired repair pathway.

Materials and Methods

The QX100 Droplet Digital PCR system (Bio-Rad) was utilized for ddPCR. TALENs were constructed using the Voytas laboratory's Golden Gate assembly system (Cermak et al., Nucleic Acids Res. 39, e82, 2011), and the MR015 backbone vector (gift from M. Porteus and M. Randar, Stanford University). Guide RNAs (gRNAs) were constructed using the Zhang laboratory's pX335 (nickase) and pX330 (nuclease) (Ran et al., Cell 154, 1380-1389, 2013). Probes and primers were from Integrated DNA Technologies.

HDR and NHEJ in Single Cells

Figures 9A, 9B:
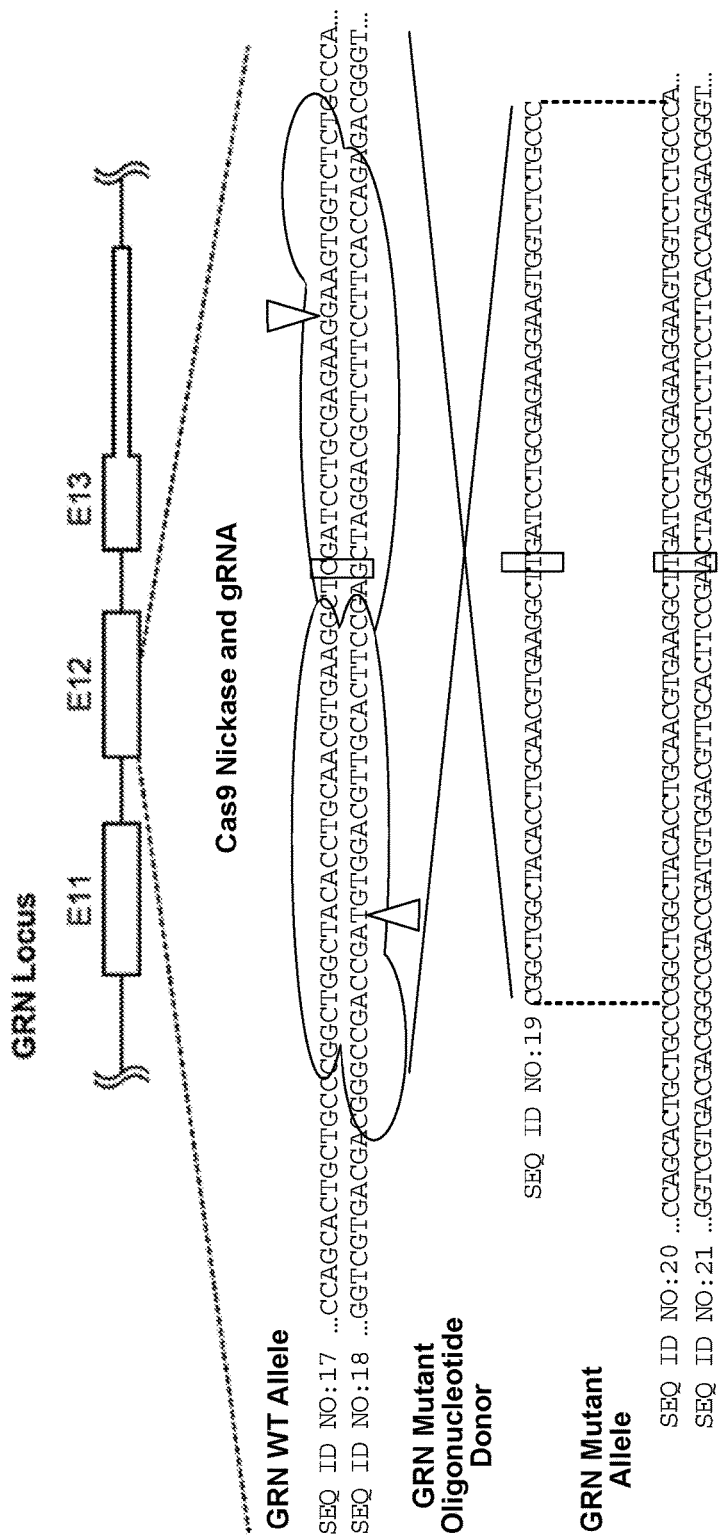
FIG. 9A-B illustrates a scheme for targeting the GRN locus for introduction of a point mutation (SEQ ID NOS: 20-21). A pair of guide RNAs (gRNAs) for Cas9 nickase were designed to localize a Cas9 nickase in two proximal positions in the GRN locus (SEQ ID NOS:17-18) to generate a pair of proximal single stranded nicks on opposite strands of the target locus. A donor oligonucleotide (SEQ ID NO: 19) encoding the desired mutation can act as a template during homology directed repair (HDR) of the lesion.

FIG. 9A-B illustrate a strategy for targeting the GRN locus for point mutagenesis in human induced pluripotent stem (iPS) cells. A pair of gRNAs for Cas9 nickase were designed to introduce a C>T point mutation in the GRN locus (FIG. 9A). The wild-type C (SEQ ID NO:17-18) and mutant T (SEQ ID NO:20-21) residues are highlighted by rectangles. The nick sites are indicated by triangles. Sequences of an isolated iPS cell clone were aligned to the WT sequence (SEQ ID NOS:22-24) (FIG. 9B). This clone had the C>T point mutation (SEQ ID NO:23) and a 24-bp deletion (SEQ ID NO:24). These results indicate that HDR and NHEJ can happen in single cells, ending up in compound heterozygous mutant cells.

Design of Targeting and Detection of HDR

Figure 10A:
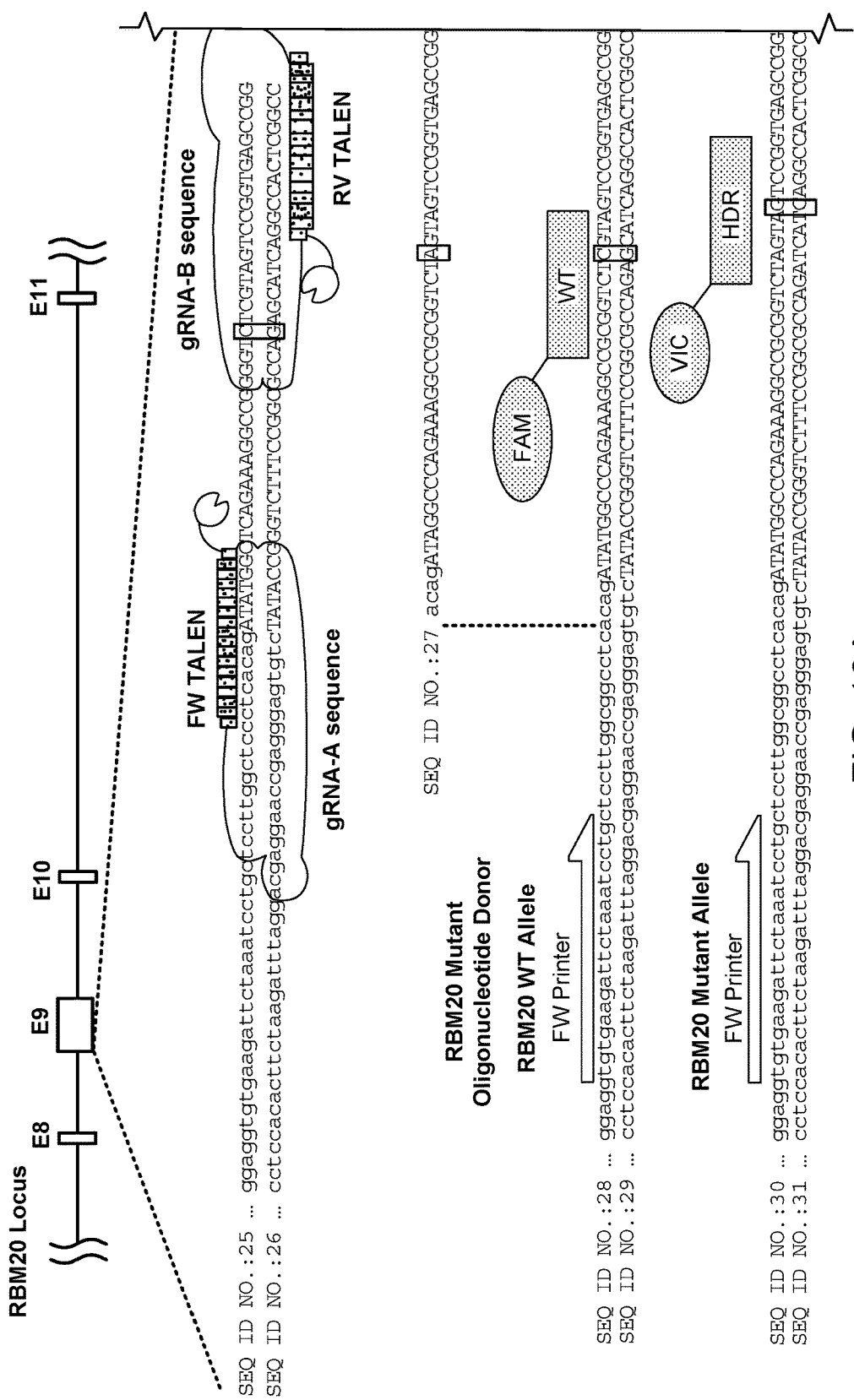

FIG. 10A-B illustrate a strategy for targeting and detection of homology directed repair (HDR) mutations in cells. FIG. 10A depicts the design of the TALEN, CRISPR/Cas9, and TaqMan PCR systems for mutagenesis at the RBM20 locus. A pair of TALENs and a pair of gRNAs (SEQ ID NOS:25-26) were designed. A 60-nt donor oligonucleotide (SEQ ID NO:27) that has a C>A mutation as compared to the wild-type sequence (SEQ ID NOS:28-29) was designed to act as a template for HDR repair, thereby introducing the C>A mutation into a cell (SEQ ID NOS:30-31). An allelic-specific TaqMan PCR assay, designed to detect specific edits induced by HDR but not detect NHEJ, is also depicted. In this assay, a carboxyfluorescein labeled probe complementary to the wild-type sequence is utilized to detect the wild-type sequence and a VIC labeled probe complementary to the HDR mutant sequence encoded by the donor oligonucleotide is utilized to detect wild-type and HDR mutations respectively. As shown in FIG. 10B, the following different nuclease platforms that were compared in this study: CRISPR/Cas9, CRISPR/Cas9 nickase, and TALEN to compare their activities to induce HDR and NHEJ.

ddPCR Assay to Detect Only HDR

Figure 11A:
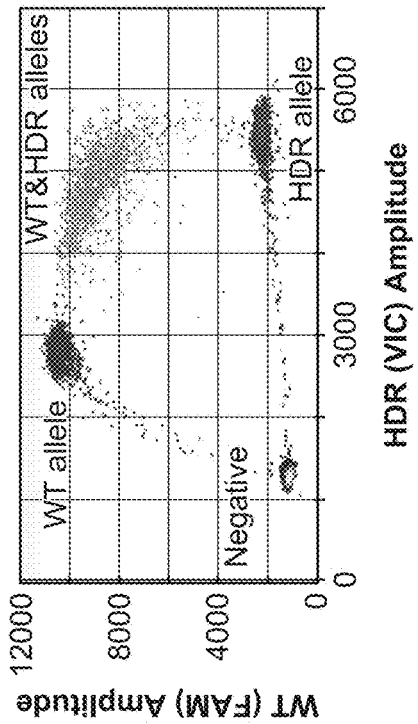
FIG. 11A-C depicts a ddPCR assay for detection of HDR mutations.
Figure 11B:
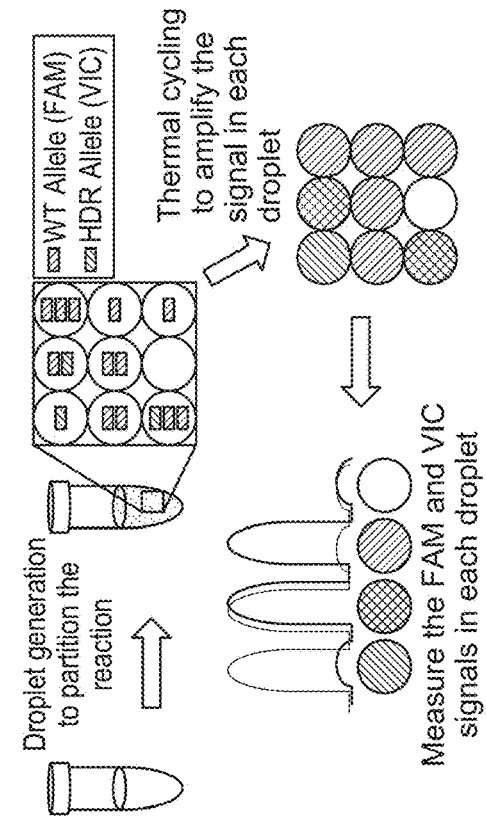
Figure 11C:
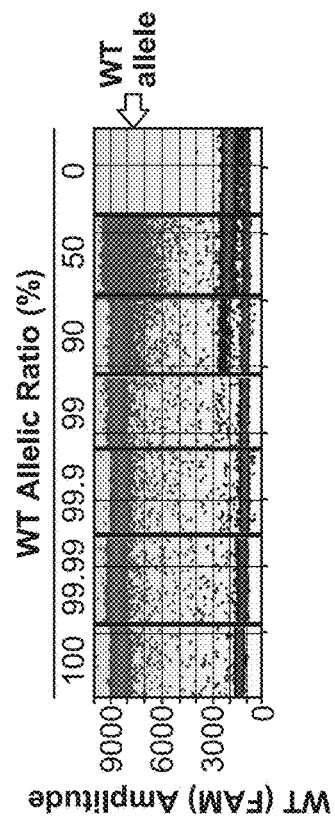
Figure 11C:
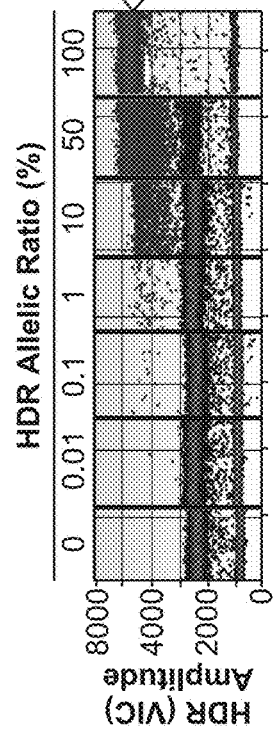

FIG. 11A-C illustrate the basics of a ddPCR assay for detection of HDR only. The reaction is partitioned into over 10,000 nanoliter water-in-oil droplets. Each droplet contains all the PCR reagents and a few or no copies of template DNA. Thermal cycling amplifies the FAM, VIC, or both signals in each droplet depending on the templates present. Finally, the signals are measured in individual droplets, allowing detection of rare templates. Concentration is reported in copies/W. FIG. 11B depicts a two-dimensional plot of ddPCR for a 1:1 mixture of the WT and HDR allele. The numbers of negative (black), FAM+ (WT allele), VIC+ (HDR allele), and FAM and VIC double+ (WT and HDR alleles) droplets are used to calculate the concentrations of the alleles. FIG. 11C depicts ddPCR data for a dilution series of the HDR allele and the WT allele. Plasmids with the WT– or HDR allele were mixed at different ratios. ddPCR can be used to robustly detect 0.1% or fewer HDR alleles in a population of WT alleles.

ddPCR Assay to Detect HDR and NHEJ

Figure 12:
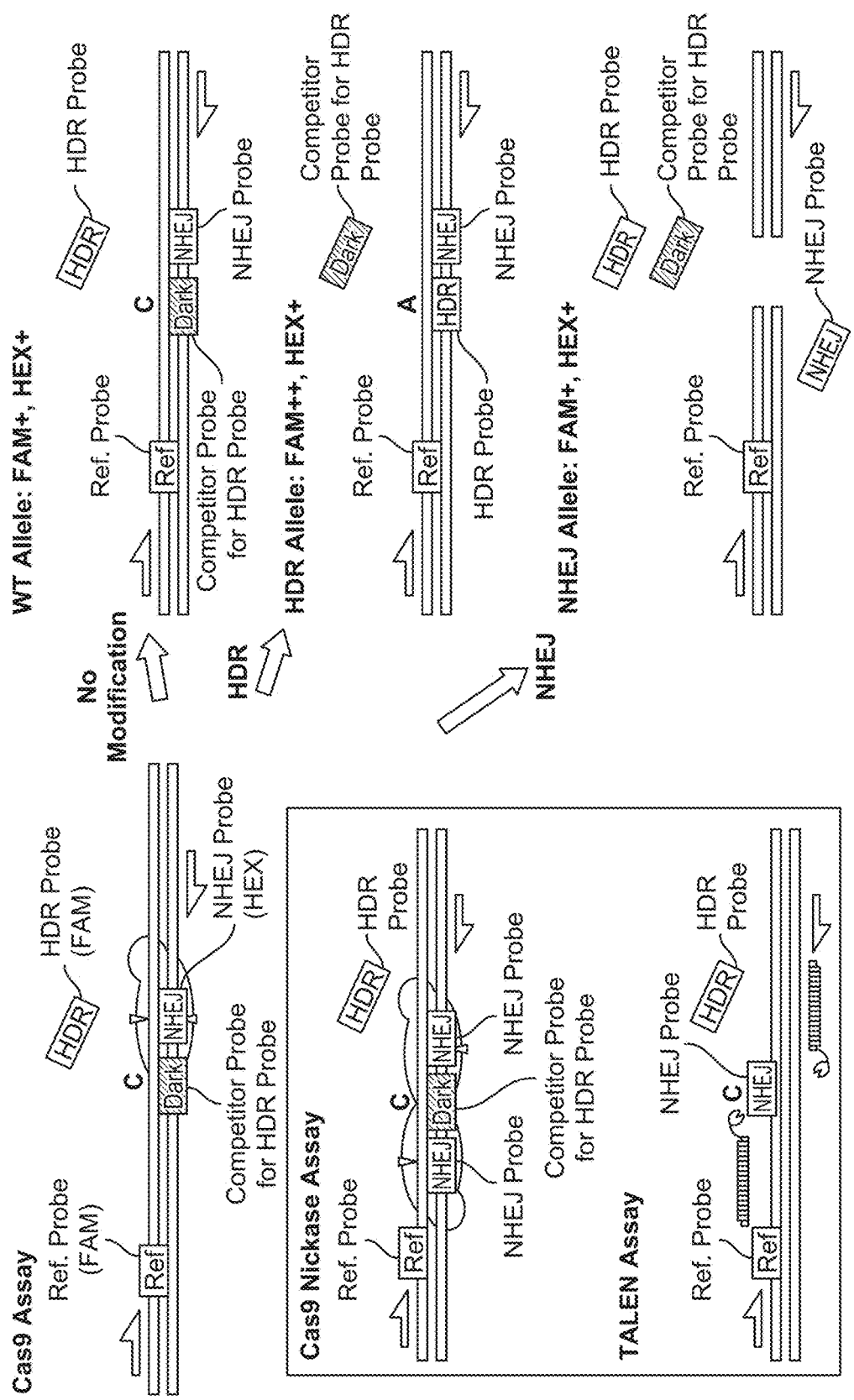
FIG. 12 depicts a scheme for a ddPCR assay to simultaneously detect both HDR and NHEJ mutations.

FIG. 12 illustrates a design for a ddPCR assay for simultaneous detection of HDR and NHEJ. An assay for detection of Cas9 mutagenesis is shown as an example. In this example, the assay utilizes a FAM-conjugated reference probe (Ref. probe) that detects a conserved sequence in the amplicon that is distal from the mutagenesis site, a FAM-conjugated HDR probe with the point mutant allele sequence that detects HDR events, a HEX-conjugated NHEJ probe located at the cut site with the conserved sequence that detects NHEJ events (or HDR events in the NHEJ probe binding region) when it fails to bind, and a Dark non-extendable competitor probe with the conserved sequence at the HDR site but lacking fluorophore. After mutagenesis to induce the RBM20 point mutation shown in FIG. 10A-B, if no modification was left, the WT allele would stay intact, giving FAM+ and HEX+ because the Ref probe and NHEJ probe bind to the WT allele. The Dark probe competes with HDR probe preventing HDR probe from binding to the WT allele. If HDR occurred to introduce the C>A conversion, HDR probe would bind to the created mutant allele instead of Dark probe, so that the HDR allele would be higher amplitude FAM++ and HEX+ as the HDR allele has two binding sites for FAM probes. If an NHEJ mutation occurs, the NHEJ probe would lose its binding site, but the Ref probe would remain bound, so that the NHEJ allele would be detected as be FAM+ and HEX-. As a result, three different types of alleles can be detected as different populations in ddPCR. Assays for Cas9 nickase and TALENs are shown in the boxed portion of FIG. 12. Since a pair of Cas9 nickases are used, the Cas9 nickase assay uses two NHEJ probes.

Validation of Assay for Simultaneous Detection of HDR and NHEJ mutations

Figure 13B:
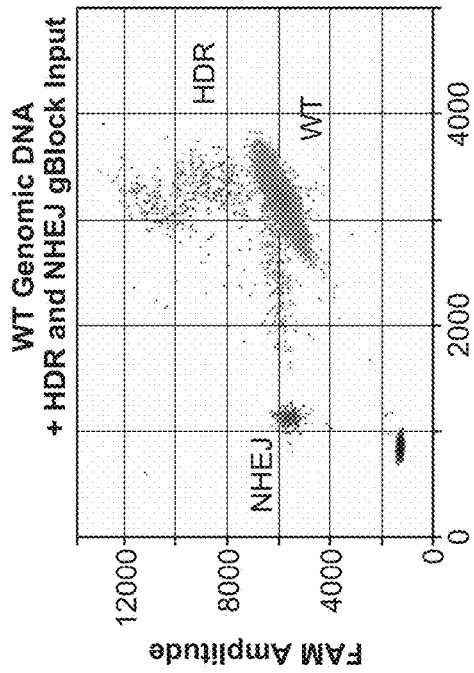
FIG. 13A-D depict data from validation of the assay depicted in FIG. 12. Genomic DNA from WT HEK293 cells without FIG. 13A and with FIG. 13B 5% gBlock DNA of HDR and NHEJ alleles were analyzed by the Cas9 probe mixture shown in FIG. 4 (Ref, HDR, NHEJ, and Dark probes).
Figure 13D:
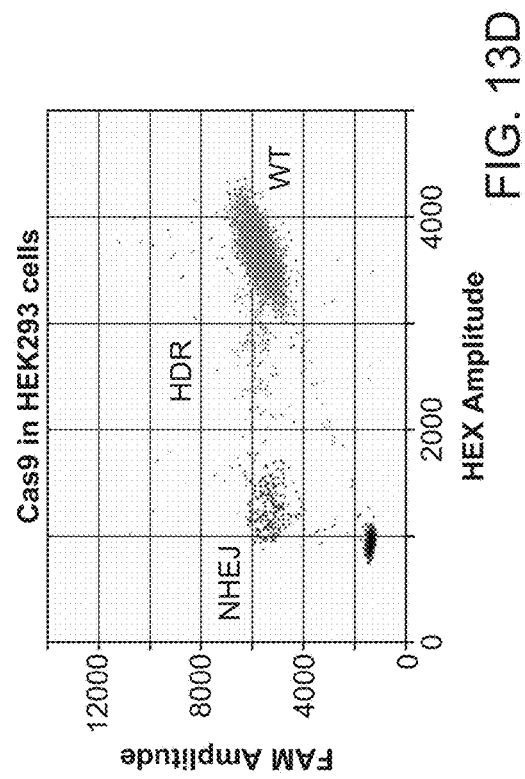
Figure 13A:
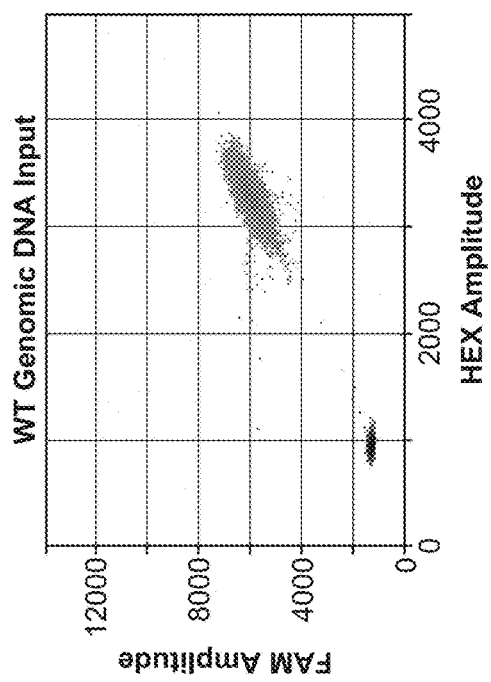
Figure 13C:
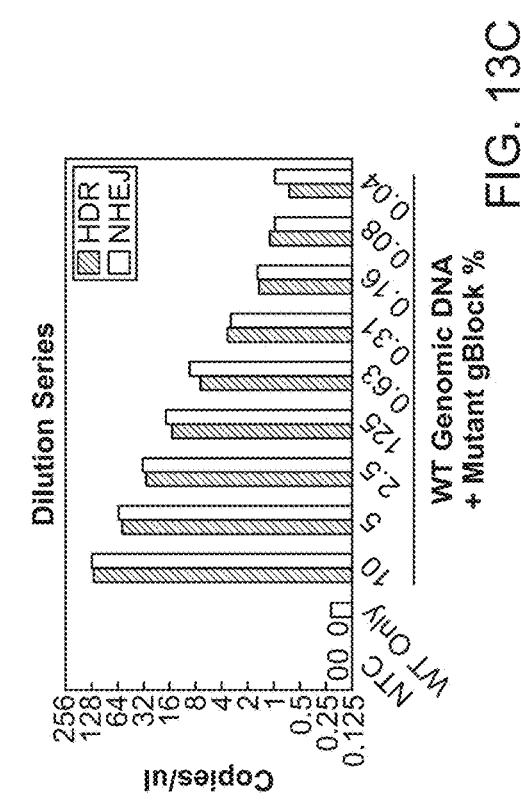

FIG. 13A-D depict validation data for a ddPCR assay to detect HDR and NHEJ induced mutations from a Cas9-based genome editing reagent with synthesized DNA (gBlock). Genomic DNA from WT HEK293 cells without (FIG. 13A) and with (FIG. 13B) 5% gBlock DNA of HDR and NHEJ alleles were analyzed by the Cas9 probe mixture shown in FIG. 12 (Ref., HDR, NHEJ, and Dark probes). All alleles were FAM+ and HEX+ in the WT genomic DNA sample, but HDR (brown) and NHEJ (blue) alleles were detected when the gBlock DNA was added. Measurement of the quantitative performance of the HDR and NHEJ assay with synthesized DNA shows that the limit of quantification was around 0.1% for detection of NHEJ mutations and lower than 0.04% for detection of HDR mutations (FIG. 13C). HEK293 cells were treated with Cas9 to induce HDR as shown in FIG. 10A, and their genomic DNA was analyzed. Both HDR+ and NHEJ+ populations were observed (FIG. 13D).

Comparison of Different Nucleases

Figure 14:
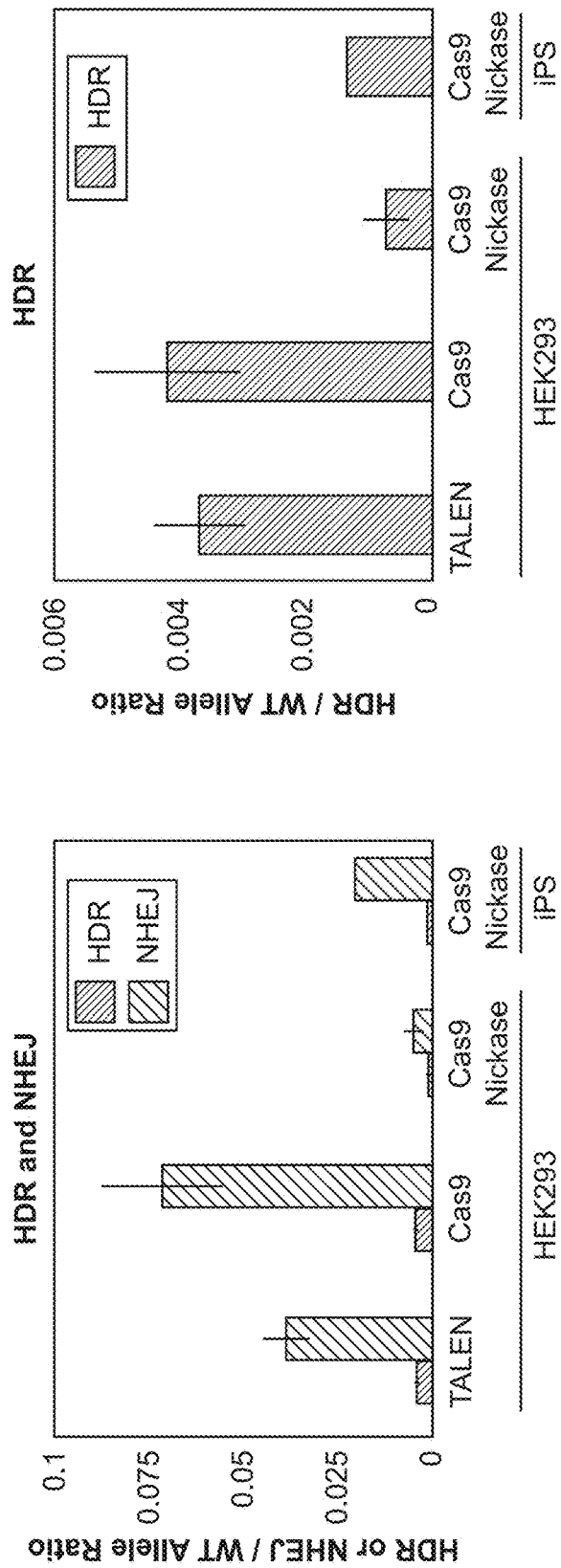
FIG. 14 depicts a comparison of the HDR and NHEJ mutation generating activities of various genome editing strategies. HEK293 cells or human iPS cells were transfected with RBM20 TALENs, Cas9, or Cas9 nickases together with an RBM20 R636S single strand DNA oligonucleotide donor to introduce the C>A mutation as shown in FIG. 10A.

HEK293 cells or human iPS cells were transfected with RBM20 TALENs, Cas9, or Cas9 nickases together with an RBM20 R636S single strand oligo DNA donor to introduce the C>A mutation as shown in FIG. 10A-B. Genomic DNA isolated from these cells were analyzed by using the probe and primer sets described in FIGS. 12 and 13 to detect HDR and NHEJ mutations. The copy numbers of the HDR and NHEJ alleles normalized to that of the WT allele are shown in FIG. 14, left graph. FIG. 14, right graph shows the data for HDR mutations only. All the nucleases induced much more NHEJ than HDR in both HEK293 cells and iPS cells.

CONCLUSION

Described herein is a highly sensitive, quantitative, and rapid method to simultaneously detect HDR and NHEJ events. By using this method, sequence-specific nucleases are shown to induce much more NHEJ than HDR. This method can enable a facile search for improved genome editing conditions. For example, the assay can be used to identify conditions that increase the generation of HDR mutations while minimizing the generation of NHEJ mutations.

What is claimed is:

1. A method for simultaneous quantification of homology directed repair (HDR) and non-homologous end joining (NHEJ) genome editing products in a sample of cells, wherein said sample of cells comprises cells that have been contacted with a site-specific genome editing reagent configured to cleave or nick DNA in a target genomic region and an HDR template nucleic acid, the method comprising:
   a) forming a plurality of mixture partitions having an average volume, wherein the mixture partitions comprise:
      i) the target genomic region;
      ii) a DNA-dependent DNA polymerase;
      iii) a forward and a reverse oligonucleotide amplification primer, wherein the forward and reverse primers hybridize to opposite strands of, and flank, the target genomic region, and wherein the primers are configured to amplify the target genomic region in the presence of the polymerase;
      iv) a detectably labeled oligonucleotide reference probe, wherein the reference probe hybridizes to a wild-type target genomic region, a target genomic region containing an HDR mutation introduced by homology directed repair of DNA damage from the site specific genome editing reagent, and a target genomic region containing an NHEJ mutation introduced by NHEJ repair of DNA damage from the site specific genome editing reagent;
      v) a detectably labeled oligonucleotide HDR probe, wherein the HDR probe hybridizes to the target genomic region containing the HDR mutation; and
      vi) a detectably labeled oligonucleotide NHEJ drop-off probe, wherein the NHEJ drop-off probe hybridizes to the wild-type target genomic region, and wherein the NHEJ drop-off probe does not hybridize to the target genomic region containing the NHEJ mutation;
   b) amplifying the target genomic region in the plurality of mixture partitions; and
   c) determining a quantity of wild-type target genomic regions, a quantity of target genomic regions containing an HDR mutation, and a quantity of target genomic regions containing an NHEJ mutation by detecting hybridization of the labeled probes to the target genomic regions in the plurality of mixture partitions.

2. The method of claim 1, wherein the reference and HDR probes comprise the same detectable label.

3. The method of claim 1, wherein the HDR probe does not hybridize to the wild-type target genomic region.

4. The method of claim 1, wherein the NHEJ drop off probe does not hybridize to the target genomic region containing the HDR mutation.

5. The method of claim 1, wherein the NHEJ drop off probe hybridizes to the target genomic region containing the HDR mutation.

6. The method of claim 1, wherein the DNA dependent DNA polymerase comprises 5' to 3' exonuclease activity and c) comprises detecting an increase in fluorescence caused by 5' to 3' exonuclease digestion of the hybridized labeled probes in the plurality of mixture partitions.

7. The method of claim 1, wherein the plurality of mixture partitions further comprise an HDR dark oligonucleotide probe, wherein the HDR dark probe comprises a 3' end that is not extendable by the DNA polymerase, and wherein the HDR dark probe competes for hybridization of the HDR probe to the wild-type target genomic region.

8. The method of claim 1, wherein the site-specific genome editing reagent is a CRISPR-Cas9 reagent, a TALEN, or a Zinc-Finger Nuclease.

9. The method of claim 1, wherein the site-specific genome editing reagent comprises two site-specific genome nickases, wherein each nickase is configured to nick target DNA in the genome of a cell within less than about 1 kb of the other nickase.

10. The method of claim 1, wherein the method comprises, before the forming the plurality of mixture partitions, providing the sample of cells and extracting the target genomic regions.

11. The method of claim 10, wherein the providing comprises contacting a plurality of cells with the site-specific genome editing reagent.

12. The method of claim 11, wherein the providing further comprises contacting the plurality of cells with an HDR template nucleic acid, wherein the HDR template nucleic acid comprises a mutation of a portion of the target genomic region and is configured to function as a template during homology directed repair of the target genomic region and thereby introduce the HDR mutation into the target genomic region.

13. The method of claim 12, wherein the HDR template nucleic acid comprises DNA.

14. The method of claim 1, wherein the plurality of mixture partitions comprise a plurality of structurally different detectably labeled oligonucleotide NHEJ drop-off probes, wherein the plurality of structurally different NHEJ drop-off probes hybridize to different sub-regions of the wild-type target genomic region.

15. The method of claim 14, wherein the plurality of structurally different NHEJ drop off probes do not hybridize to NHEJ mutated sub-regions.

16. The method of claim 14, wherein the plurality of structurally different NHEJ drop off probes do not hybridize to NHEJ mutated sub-regions and do not hybridize to HDR mutated sub-regions.

17. The method of claim 14, wherein the plurality of structurally different NHEJ drop off probes do not hybridize to NHEJ mutated sub-regions and do hybridize to target genomic regions containing an HDR mutation.

18. A method for identifying an optimized condition for genome editing of a cell, the method comprising:
   a) performing site specific genome editing of a plurality of cells under a first set of conditions to provide first sample of cells;
   b) performing site specific genome editing of a plurality of cells under a second set of conditions to provide a second sample of cells;
   c) performing the method of claim 1 to quantify a number of NHEJ edited target genomic regions and HDR edited target genomic regions in the first and second samples of cells to determine a genome editing efficiency for the first and second set of conditions;
   d) comparing the genome editing efficiency of the first and second set of conditions to identify a set of conditions that provides a higher genome editing efficiency; and
   e) selecting the set of conditions that provides higher genome editing efficiency as the optimized condition for genome editing.

19. The method of claim 18, wherein
   a) comprises contacting the first sample of cells with a first concentration of genome editing reagent; and
   b) comprises contacting the second sample of cells with a second concentration of genome editing reagent.

20. The method of claim 18, wherein
a) comprises contacting the first sample of cells with a first genome editing reagent; and
b) comprises contacting the second sample of cells with a second structurally different genome editing reagent.

21. The method of claim 1, wherein the sample of cells is from a patient to whom genome edited cells have been administered, and the method further comprises estimating a number of genome edited cells in the patient from the quantity of wild-type target genomic regions, quantity of target genomic regions containing an HDR mutation, and/or a quantity of target genomic regions containing an NHEJ mutation.

* * * * *

SEQUENCE LISTING

```
<160> NUMBER OF SEQ ID NOS: 31

<210> SEQ ID NO 1
<211> LENGTH: 49
<212> TYPE: DNA
<213> ORGANISM: Artificial Sequence
<220> FEATURE:
<223> OTHER INFORMATION: synthetic nucleotide sequence - DNA target

<400> SEQUENCE: 1
aatggggagg acatcgatgt cacctccaat gactagggtg ggcaaccac                49

<210> SEQ ID NO 2
<211> LENGTH: 49
<212> TYPE: DNA
<213> ORGANISM: Artificial Sequence
<220> FEATURE:
<223> OTHER INFORMATION: synthetic nucleotide sequence - DNA target
      (reverse complement)

<400> SEQUENCE: 2
gtggttgccc accctagtca ttggaggtga catcgatgtc ctccccatt                49

<210> SEQ ID NO 3
<211> LENGTH: 101
<212> TYPE: DNA
<213> ORGANISM: Artificial Sequence
<220> FEATURE:
<223> OTHER INFORMATION: synthetic nucleotide sequence - sgRNA

<400> SEQUENCE: 3
gtcacctcca atgactaggg guuuuagagc uagaauagca aguuaaaaua aggcuagucc    60
```
guuaucaacu ugaaaaagug gcaccgaguc ggugcuuuuu u          101

<210> SEQ ID NO 4
<211> LENGTH: 60
<212> TYPE: DNA
<213> ORGANISM: Artificial Sequence
<220> FEATURE:
<223> OTHER INFORMATION: synthetic nucleotide sequence - donor oligo

<400> SEQUENCE: 4
acagatatgg cccagaaagg ccgcggtcta gtagtccggt gagccggtca ctctccccga          60

<210> SEQ ID NO 5
<211> LENGTH: 46
<212> TYPE: DNA
<213> ORGANISM: Artificial Sequence
<220> FEATURE:
<223> OTHER INFORMATION: synthetic gRNA oligonucleotide sequence

<400> SEQUENCE: 5
ccttggctcc ctcacagata tggggtctcg tagtccggtg agccgg          46

<210> SEQ ID NO 6
<211> LENGTH: 23
<212> TYPE: DNA
<213> ORGANISM: Artificial Sequence
<220> FEATURE:
<223> OTHER INFORMATION: synthetic gRNA oligonucleotide sequence

<400> SEQUENCE: 6
ggtctcgtag tccggtgagc cgg          23

<210> SEQ ID NO 7
<211> LENGTH: 87
<212> TYPE: DNA
<213> ORGANISM: Artificial Sequence
<220> FEATURE:
<223> OTHER INFORMATION: synthetic gRNA oligonucleotide sequence

<400> SEQUENCE: 7
taaatcctgc tccttggctc cctcacagat atgggcccaga aaggccgcgg tctcgtagtc          60
cggtgagccg gtcactctcc ccgaggt          87

<210> SEQ ID NO 8
<211> LENGTH: 16
<212> TYPE: DNA
<213> ORGANISM: Artificial Sequence
<220> FEATURE:
<223> OTHER INFORMATION: synthetic primer oligonucleotide

<400> SEQUENCE: 8
gtcctctgca cggaag          16

<210> SEQ ID NO 9
<211> LENGTH: 16
<212> TYPE: DNA
<213> ORGANISM: Artificial Sequence
<220> FEATURE:
<223> OTHER INFORMATION: synthetic oligonucleotide probe HEX (NHEJ)

<400> SEQUENCE: 9
tgctccttgg ctccct          16

<210> SEQ ID NO 10

```
<211> LENGTH: 17
<212> TYPE: DNA
<213> ORGANISM: Artificial Sequence
<220> FEATURE:
<223> OTHER INFORMATION: synthetic oligonucleotide probe FAM (HDR)

<400> SEQUENCE: 10
ccgcggtcta gtagtcc                                                    17

<210> SEQ ID NO 11
<211> LENGTH: 16
<212> TYPE: DNA
<213> ORGANISM: Artificial Sequence
<220> FEATURE:
<223> OTHER INFORMATION: synthetic oligonucleotide probe FAM (ref)

<400> SEQUENCE: 11 accccctgggc acatga                                                    16

<210> SEQ ID NO 12
<211> LENGTH: 142
<212> TYPE: DNA
<213> ORGANISM: Artificial Sequence
<220> FEATURE:
<223> OTHER INFORMATION: synthetic oligonucleotide target sequence

<400> SEQUENCE: 12
gtcctctgca cggaagccag ataaatcctg ctccttggct ccctcacaga tatggcccag      60
aaaggccgcg gtctcgtagt ccggtgagcc ggtcactctc ccgaggttg gaccccctggg    120 cacatgatcg caaacaccac cc                                             142

<210> SEQ ID NO 13
<211> LENGTH: 142
<212> TYPE: DNA
<213> ORGANISM: Artificial Sequence
<220> FEATURE:
<223> OTHER INFORMATION: synthetic oligonucleotide target sequence
      (reverse complement)

<400> SEQUENCE: 13
gggtggtgtt tgcgatcatg tgcccagggg tccaacctcg gggagagtga ccggctcacc      60
ggactacgag accgcggcct ttctgggcca tatctgtgag ggagccaagg agcaggattt    120
atctggcttc cgtgcagagg ac                                             142

<210> SEQ ID NO 14
<211> LENGTH: 15
<212> TYPE: DNA
<213> ORGANISM: Artificial Sequence
<220> FEATURE:
<223> OTHER INFORMATION: synthetic primer oligonucleotide

<400> SEQUENCE: 14
gggtggtgtt tgcga                                                      15

<210> SEQ ID NO 15
<211> LENGTH: 16
<212> TYPE: DNA
<213> ORGANISM: Artificial Sequence
<220> FEATURE:
<223> OTHER INFORMATION: synthetic oligonucleotide probe HEX (NHEJ)

<400> SEQUENCE: 15
agagtgaccg gctcac                                                     16
```

<210> SEQ ID NO 16
<211> LENGTH: 15
<212> TYPE: DNA
<213> ORGANISM: Artificial Sequence
<220> FEATURE:
<223> OTHER INFORMATION: synthetic oligonucleotide probe HEX (NHEJ)

<400> SEQUENCE: 16
cggcctttct gggcc                                                    15

<210> SEQ ID NO 17
<211> LENGTH: 75
<212> TYPE: DNA
<213> ORGANISM: Artificial Sequence
<220> FEATURE:
<223> OTHER INFORMATION: synthetic nucleotide GRN WT Allele

<400> SEQUENCE: 17
ccagcactgc tgcccggctg gctacacctg caacgtgaag gctcgatcct gcgagaagga    60
agtggtctct gccca                                                    75

<210> SEQ ID NO 18
<211> LENGTH: 75
<212> TYPE: DNA
<213> ORGANISM: Artificial Sequence
<220> FEATURE:
<223> OTHER INFORMATION: synthetic nucleotide GRN WT Allele (reverse
      complement)

<400> SEQUENCE: 18
tgggcagaga ccacttcctt ctcgcaggat cgagccttca cgttgcaggt gtagccagcc    60
gggcagcagt gctgg                                                    75

<210> SEQ ID NO 19
<211> LENGTH: 60
<212> TYPE: DNA
<213> ORGANISM: Artificial Sequence
<220> FEATURE:
<223> OTHER INFORMATION: synthetic GRN Mutant Oligonucleotide Donor

<400> SEQUENCE: 19
cggctggcta cacctgcaac gtgaaggctt gatcctgcga aggaagtg gtctctgccc    60

<210> SEQ ID NO 20
<211> LENGTH: 75
<212> TYPE: DNA
<213> ORGANISM: Artificial Sequence
<220> FEATURE:
<223> OTHER INFORMATION: synthetic nucleotide GRN mutant allele

<400> SEQUENCE: 20
ccagcactgc tgcccggctg gctacacctg caacgtgaag gcttgatcct gcgagaagga    60
agtggtctct gccca                                                    75

<210> SEQ ID NO 21
<211> LENGTH: 75
<212> TYPE: DNA
<213> ORGANISM: Artificial Sequence
<220> FEATURE:
<223> OTHER INFORMATION: synthetic nucleotide GRN mutant allele
      (reverse complement)

<400> SEQUENCE: 21
tgggcagaga ccacttcctt ctcgcaggat caagccttca cgttgcaggt gtagccagcc    60

```
gggcagcagt gctgg                                                     75

<210> SEQ ID NO 22
<211> LENGTH: 66
<212> TYPE: DNA
<213> ORGANISM: Artificial Sequence
<220> FEATURE:
<223> OTHER INFORMATION: synthetic oligonucleotide - WT

<400> SEQUENCE: 22
gctgcccggc tggctacacc tgcaacgtga aggctcgatc ctgcgagaag gaagtggtct    60
ctgccc                                                               66

<210> SEQ ID NO 23
<211> LENGTH: 66
<212> TYPE: DNA
<213> ORGANISM: Artificial Sequence
<220> FEATURE:
<223> OTHER INFORMATION: synthetic oligonucleotide - Allele A

<400> SEQUENCE: 23
gctgcccggc tggctacacc tgcaacgtga aggcttgatc ctgcgagaag gaagtggtct    60
ctgccc                                                               66

<210> SEQ ID NO 24
<211> LENGTH: 42
<212> TYPE: DNA
<213> ORGANISM: Artificial Sequence
<220> FEATURE:
<223> OTHER INFORMATION: synthetic oligonucleotide - Allele B

<400> SEQUENCE: 24
gctgcccggc tggctacacc tgcaaggaag tggtctctgc cc                       42

<210> SEQ ID NO 25
<211> LENGTH: 132
<212> TYPE: DNA
<213> ORGANISM: Artificial Sequence
<220> FEATURE:
<223> OTHER INFORMATION: synthetic gRNA nucleotide sequence

<400> SEQUENCE: 25
ggaggtgtga agattctaaa tcctgctcct tggctccctc acagatatgg ctcagaaagg    60
ccggggtctc gtagtccggt gagccggtca ctctccccga ggtcccacac tcccagcttc   120
acctcctgca gc                                                       132

<210> SEQ ID NO 26
<211> LENGTH: 132
<212> TYPE: DNA
<213> ORGANISM: Artificial Sequence
<220> FEATURE:
<223> OTHER INFORMATION: synthetic gRNA nucleotide sequence (reverse
      complement)

<400> SEQUENCE: 26
gctgcaggag gtgaagctgg gagtgtggga cctcggggag agtgaccggc tcaccggact    60
acgagacccc ggcctttctg agccatatct gtgagggagc caaggagcag gatttagaat   120
cttcacacct cc                                                       132

<210> SEQ ID NO 27
<211> LENGTH: 60
```

```
<212> TYPE: DNA
<213> ORGANISM: Artificial Sequence
<220> FEATURE:
<223> OTHER INFORMATION: synthetic donor oligonucleotide sequence

<400> SEQUENCE: 27
acagatatgg cccagaaagg ccgcggtcta gtagtccggt gagccggtca ctctccccga    60

<210> SEQ ID NO 28
<211> LENGTH: 132
<212> TYPE: DNA
<213> ORGANISM: Artificial Sequence
<220> FEATURE:
<223> OTHER INFORMATION: synthetic RMB20 WT Allele nucleotide sequence

<400> SEQUENCE: 28
ggaggtgtga agattctaaa tcctgctcct tggcggcctc acagatatgg cccagaaagg    60
ccgcggtctc gtagtccggt gagccggtca ctctccccga ggtcccacac tccgagcttc   120
acctcctgca gc                                                       132

<210> SEQ ID NO 29
<211> LENGTH: 132
<212> TYPE: DNA
<213> ORGANISM: Artificial Sequence
<220> FEATURE:
<223> OTHER INFORMATION: synthetic RMB20 WT Allele nucleotide sequence
      (reverse
      complement)

<400> SEQUENCE: 29
gctgcaggag gtgaagctcg gagtgtggga cctcggggag agtgaccggc tcaccggact    60
acgagaccgc ggcctttctg ggccatatct gtgaggccgc caaggagcag gatttagaat   120
cttcacacct cc                                                       132

<210> SEQ ID NO 30
<211> LENGTH: 132
<212> TYPE: DNA
<213> ORGANISM: Artificial Sequence
<220> FEATURE:
<223> OTHER INFORMATION: synthetic RMB20 Mutant Allele nucleotide
      sequence

<400> SEQUENCE: 30
ggaggtgtga agattctaaa tcctgctcct tggcggcctc acagatatgg cccagaaagg    60
ccgcggtcta gtagtccggt gagccggtca ctctccccga ggtcccacac tccgagcttc   120
acctcctgca gc                                                       132

<210> SEQ ID NO 31
<211> LENGTH: 132
<212> TYPE: DNA
<213> ORGANISM: Artificial Sequence
<220> FEATURE:
<223> OTHER INFORMATION: synthetic RMB20 Mutant Allele nucleotide
      sequence (reverse complement)

<400> SEQUENCE: 31
gctgcaggag gtgaagctcg gagtgtggga cctcggggag agtgaccggc tcaccggact    60
actagaccgc ggcctttctg ggccatatct gtgaggccgc caaggagcag gatttagaat   120
cttcacacct cc                                                       132
```